United States Patent [19]

Dombek

[11] 4,434,247

[45] Feb. 28, 1984

[54] CONTINUOUS PROCESS FOR THE MANUFACTURE OF ETHYLENE GLYCOL

[75] Inventor: Bernard D. Dombek, Charleston, W. Va.

[73] Assignee: Union Carbide Corporation, Danbury, Conn.

[21] Appl. No.: 358,703

[22] Filed: Mar. 16, 1982

Related U.S. Application Data

[63] Continuation of Ser. No. 190,988, Sep. 26, 1980, abandoned, which is a continuation-in-part of Ser. No. 91,242, Nov. 15, 1979, abandoned, which is a continuation-in-part of Ser. No. 971,667, Dec. 21, 1978, abandoned, and Ser. No. 971,816, Dec. 21, 1978, abandoned.

[51] Int. Cl.$^3$ .............................................. C07C 27/06
[52] U.S. Cl. ................................................... 518/700
[58] Field of Search ......................................... 518/700

[56] References Cited

U.S. PATENT DOCUMENTS

| | | | |
|---|---|---|---|
| 2,534,018 | 12/1950 | Gresham et al. | 260/449.6 |
| 2,535,060 | 12/1950 | Gresham | 264/449 |
| 2,549,470 | 4/1951 | Howk et al. | 260/449 |
| 2,636,046 | 4/1953 | Gresham | 260/449.6 |
| 3,110,747 | 11/1963 | Mullineaux | 260/683.9 |
| 3,285,948 | 11/1966 | Butter | 260/642 |
| 3,539,634 | 11/1970 | Olivier et al. | 260/694 |
| 3,579,566 | 5/1971 | Fenton | 260/488 |
| 3,833,634 | 9/1974 | Pruett et al. | 260/449 R |
| 3,957,857 | 5/1976 | Pruett et al. | 260/449 |
| 4,133,966 | 1/1979 | Pretzer et al. | 568/902 |
| 4,162,261 | 7/1979 | Kaplan . | |
| 4,170,605 | 10/1979 | Williamson et al. | 260/449 |

FOREIGN PATENT DOCUMENTS

2644185 4/1977 Fed. Rep. of Germany .

OTHER PUBLICATIONS

Pruett, Roy L., Annls. New York Academy of Sciences, vol. 295, pp. 239-248 (1977).
Fonseca, R. et al. High Pressure Science and Technology, 6th AIRAPT Conference (Chapt. "High Pressure Synthesis of Polyalcohols by Catalytic Hydrogenation of Carbon Monoxide") pp. 733-738, Plenum Press, N.Y. (1979).
Deluzarche, A. et al. Erdol and Kohle-Erdgas-Petrochemie vereinigt mit Brennstoff-Chemie, Bdg. 32, Heft 7, pp. 313-316 (Jul. 1979).
Catalytica Letters, vol. 5 No. 1 (1/79) reporting on J. S. Bradley Paper No. 54 of the 1st. Int. Symp. on Homogeneous Catalysis held at Corpus Christi, Tex. on 11/29 through 12/1/78.
J. W. Rathke and H. M. Feder, J. Amer. Chem. Soc., 100 (11) pp. 3623-3625 (May 24, 1978).
Japanese Patent Application (Kokai) No. 52-73804/77 (Derwent Abstract and Translation).
Lyons, J. C. S. Chem. Comm. pp. 412, 413 (1975).
Wender et al., Chem. and Ind. pp. 1694-1695 (1958).
Bianchi et al., Journal of Organometallic Chemistry, vol. 141, pp. 107-111 (1977).
Bianchi et al., La Chimica & L'Industrie, vol. 60, pp. 588-592 (1978), including a translation thereof.

*Primary Examiner*—Howard T. Mars
*Attorney, Agent, or Firm*—Norman L. Balmer

[57] ABSTRACT

This invention relates to the manufacture of valuable alcohols containing 1 to 2 carbon atoms, especially glycol and ethanol from the reaction of hydrogen and carbon monoxide, by a homogeneous catalytic process using as a catalyst a solubilized ruthenium carbonyl complex. The invention also encompasses the catalyst formed during the process. A particular desirable embodiment of the invention is the continuous operation thereof in a manner which minimizes inhibition of glycol formation and represses formation of adverse or undesirable glycol byproducts.

34 Claims, 1 Drawing Figure

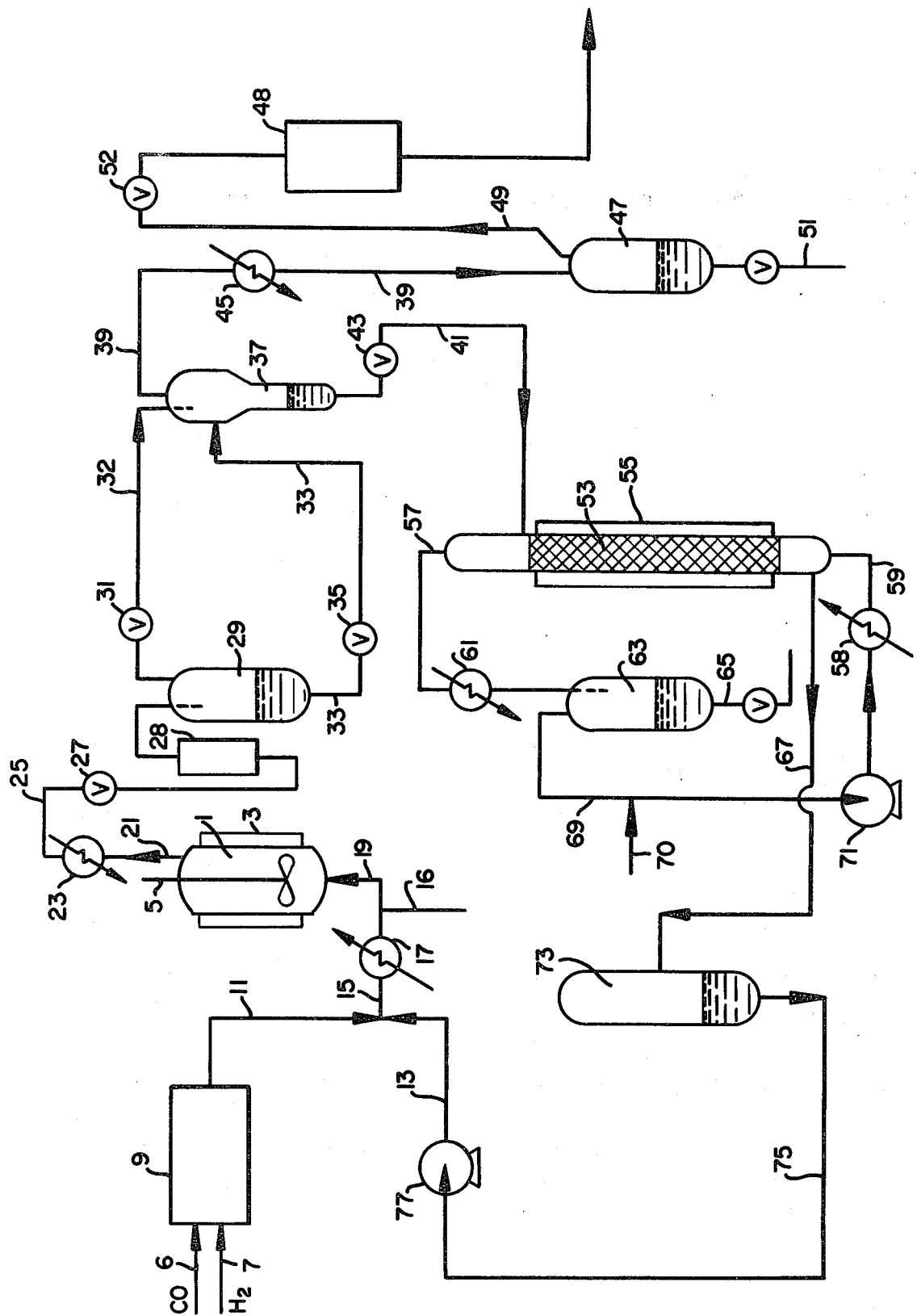

CONTINUOUS PROCESS FOR THE MANUFACTURE OF ETHYLENE GLYCOL

This application is a continuation of copending U.S. patent application Ser. No. 190,988, filed Sept. 26, 1980 abandoned which is a continuation-in-part of copending U.S. patent application Ser. Nos. 091,242, filed Nov. 15, 1979, which is a continuation-in-part of U.S. patent applications Ser. No. 971,667 and 971,816, both filed Dec. 21, 1978, all of which applications are commonly assigned and are abandoned.

This invention relates to an improved process, and the catalyst which achieves this process, for making ethylene glycol, methanol and ethanol directly from synthesis gas, i.e., mixtures of hydrogen and carbon monoxide. More particularly, this invention achieves the production of ethylene glycol directly from synthesis gas using a ruthenium carbonyl complex catalyst under process conditions which heretofore were regarded as being incapable of producing ethylene glycol with a ruthenium containing catalyst. This invention encompasses a process of producing ethylene glycol, methanol and ethanol directly from the reaction of synthesis gas in the presence of a stable ruthenium catalyst. The process of this invention is distinctive in the stability of the process, avoiding any significant loss of ruthenium values from reaction. In addition, this process features a unique ruthenium containing catalyst, possibly mononuclear, for the catalytic process which produces ethylene glycol, methanol and ethanol.

This invention also encompasses a continuous process for making the more valued product of the reaction, to wit, ethylene glycol, and includes the repeated, that is, the periodic or continuous, removal of product from the reaction zone in such a manner as to enhance the rate of production of ethylene glycol while minimizing the formation of byproduct reaction products which deplete the concentration of desired ethylene glycol.

DISCUSSION OF THE PRIOR ART

Pruett and Walker, U.S. Pat. No. 3,833,634, patented Sept. 3, 1974, based on an application originally filed Dec. 21, 1971, describe a process for preparing glycols by reacting an oxide of carbon with hydrogen using a rhodium carbonyl complex catalyst. The examples of the patent compare the reaction of hydrogen and carbon monoxide in the presence of the desired rhodium containing catalyst and other metals. In Example 9 of the patent, the reaction was attempted with triruthenium dodecacarbonyl as the catalyst using tetrahydrofuran as the solvent with a reaction temperature of 230° C., for 2 hours, and "the product contained no polyhydric alcohol." As will be shown below, Pruett and Walker apparently failed because they did not run at the conditions of reaction long enough and/or with enough ruthenium containing catalyst to achieve reaction to produce at least a detectable amount of a polyhydric alcohol such as ethylene glycol; see Example 82, infra. Example 82 employs substantially more ruthenium than did Pruett and Walker in their Example 9. Unquestionably, ruthenium is not as active a catalyst source to produce glycol as is rhodium under the conditions investigated.

Gresham, U.S. Pat. No. 2,535,060, describes a process for preparing monohydric alcohols by introducing carbon monoxide, hydrogen and a hydroxylated solvent into a reaction vessel and heating the mixture in the presence of a ruthenium-containing substance and an alkaline reagent which controls the pH within the range of 7 to 11.5, at a temperature within the range of 150° to 300° C. under a pressure within the range of 200 to 1,000 atmospheres.

Solid ruthenium dioxide is used in Examples 1 and 2 of the Gresham patent. Experimental evidence (see Example 83, infra) shows that Gresham utilized a heterogeneous reaction system.* At column 2, lines 30–33 of the patent, the patentee states his belief that ruthenium dioxide is reduced in situ during the reaction. Example 1 compares the use of a number of solutes such as phosphoric acid, acidic phosphate buffer, no solutes at all, ammonia and sodium bicarbonate. In this example, the solvent was water. In Example 2 of Gresham, a number of alcohols were characterized as solvents.

*See discussion of Howk, et al., infra, and refer to *Catalysis*, Vol. 2, 1978, pp. 67–68, published by The Chemical Society, London WIV OBN, England.

Gresham states that ruthenium and its compounds are "specific" in their effect upon this reaction and other catalysts "do not lead to straight chain primary alcohols under the conditions of this process". There is no indication that Gresham's process, as operated by him, produced ethylene glycol.

Gresham's work should be contrasted with his earlier work described in U.S. Pat. No. 2,636,046, filed Oct. 16, 1948. In this patent, Gresham describes the production of polyfunctional oxygen-containing organic products including such compounds as ethylene glycol, glycerine, and the like.* This is accomplished by the reaction of hydrogen with carbon monoxide in the presence of a solvent to produce glycol. According to this patent, the reaction of carbon monoxide with hydrogen must be at pressures of above 1,000 atmospheres and "particularly above a minimum of about 1,400 atmospheres" in order to obtain the "polyfunctional oxygen-containing organic compounds—in excellent yield" (column 2, lines 9–17). The patent specifically states at column 2, lines 37–43, that "[I]n the hydrogenation of oxides of carbon at pressures of 1,000 atmospheres and below, virtually no polyfunctional compounds are produced. At pressures above 1,000 atmospheres and especially at pressures of about 1,500 to 5,000 atmospheres preferably 2,000 to 5,000 atmospheres, polyfunctional compounds are obtained."

Though the examples of the patent describe the use only of cobalt catalyst, the patentee, at column 3, line 61, indicates that the catalyst may contain "cobalt, ruthenium, etc." According to the patentee, the most outstanding results are obtained by using a catalyst containing cobalt, especially compounds of cobalt which are soluble in at least one of the ingredients of the reaction mixture.

*Note the evaluation of this work by Rathke and Feder, JACS, 100, pp. 3623–3625 (May 24, 1978).

According to Roy L. Pruett, *Annals, New York Academy of Sciences*, Vol. 295, pages 239–248 (1977), at page 245, metals other than rhodium were tested to determine the production of ethylene glycol from mixtures of carbon monoxide and hydrogen. These metals include cobalt, ruthenium, copper, manganese, iridium and platinum. Of these metals, only cobalt was found to have a slight activity, citing British Pat. No. 665,698 which corresponds generally to the last mentioned Gresham U.S. Patent. Pruett stated that such slight activity with cobalt was "qualitatively" in agreement with the results obtained by Ziesecke, 1952, Brennstoff-Chem, 33:385.

Prior to the filing of U.S. Pat. No. 2,535,060 and subsequent to the filing of U.S. Pat. No. 2,636,046, there was filed on Apr. 12, 1949, a commonly assigned application by Howk, et al. which issued as U.S. Pat. No. 2,549,470 on Apr. 17, 1951. The Howk, et al. patent is directed to a catalytic process for making monohydric straight chain alcohols and does not mention the production of ethylene glycol. The patent emphasizes the production of straight chain primary hydroxyalkanes having from 3 to 50 or more carbon atoms in the molecule. This, the patent states, is accomplished by introducing hydrogen, carbon monoxide and a hydroxylated solvent into a reaction vessel, and heating the mixture in the presence of a catalyst of the class consisting of ruthenium metal, ruthenium oxide and ruthenium carbonyl, at a pressure within the range of 200 to 1,000 atmospheres, and at a temperature within the range of 100° to 250° C. The liquid hydroxyl-containing reaction medium may be water or alcohol, preferably a primary hydroxyalkane having from 1–10 carbon atoms per molecule. According to the patentee, a substantial proportion of the reaction product usually consists of alcohols containing more than 6 carbon atoms per molecule. The patent goes on to state (column 1, line 50, et seq.):

"The reaction products usually contain virtually no hydrocarbons, acids, esters, or branched-chain alcohols. These results were entirely unexpected, in view of the existing knowledge of the catalytic reaction between carbon monoxide and hydrogen in the presence of alcohols and Group VIII metal catalysts."

According to the Howk, et al. patent:

"It should be emphasized here that, under the conditions of temperature, pressure and gas ratios just described, no reaction takes place between carbon monoxide and hydrogen in a liquid medium (water or alcohol) if one of the common group VIII metals, such as cobalt or nickel, is used as the catalyst. This is evidenced by the fact that, using, for example, a cobalt catalyst, no significant drop in pressure is observed when carbon monoxide and hydrogen are contacted under the conditions recited. Ruthenium is thus unexpectedly different from these related metals." (Column 4, lines 19–30.)

The numbered examples indicate an apparent preference for making normal-monohydric alcohols, with the proportion of pentane soluble to pentane insoluble alcohol being at least 2:1. In one example, starting at the bottom of column 6 of Howk, et al., the solvent employed is characterized as a carboxylic acid or anhydride rather than the neutral hydroxylated solvents which were described in the other examples. This comparative example demonstrated that in a process operated at 200° C. for 18 hours using pressures maintained in the range of 300–950 atmospheres by repressurizing periodically with synthesis gas, there was produced a reaction product containing "a large quantity of wax." According to the author, 40.55 parts of esters boiling from 59° C. at atmospheric pressure to 150° C. at 116 millimeters pressure were obtained and this can be compared to the wax obtained in the amount of 37.06 parts. In that particular example, the patentee appears to have demonstrated that when one does not employ the hydroxylated solvent, the amount of wax essentially equals the amount of pentane soluble alcohol products obtained. This is supported by the statement at column 2 of Gresham U.S. Pat. No. 2,535,060 which refers to Howk, et al.

At column 3, lines 54 eq seq., Howk, et al. describe the influence that pressure has on the course of the reaction. According to Howk, et al. with pressures up to about 150 atmospheres the reaction products are only hydrocarbons. This appears to be in accord with recent work described by Masters, et al. in German Patent Application (Offenlegungsschrift) 2,644,185*, based upon British priority application Specification No. 40,322-75, filed Oct. 2, 1975. Masters, et al. obtained only hydrocarbons at such pressures using a ruthenium catalyst.

*See Doyle, et al., *J. of Organometallic Chem.*, 174, C55-C58 (1979), who conclude that the process charazterized in the German Offenlegungsschrift involved a heterogeneous Fischer-Tropsch reaction.

Fenton, U.S. Pat. No. 3,579,566, patented May 18, 1971, is concerned with a process of reducing organic acid anhydrides with hydrogen in the presence of a Group VIII noble metal catalyst and a biphyllic ligand of phosphorus, arsenic or antimony. The process of Fenton bears a remarkable similarity to oxo processing conditions to produce aldehydes and alcohols (compare with Oliver, et al., U.S. Pat. No. 3,539,634, patented Nov. 10, 1970) except that Fenton fails to supply an olefinic compound to the reaction. In the Fenton reaction, an acid anhydride, such as acetic acid anhydride, is reduced to ethylidene diacetate in the presence of hydrogen and a rhodium halide or a mixture of palladium chloride and ruthenium trichloride catalyst, provided in combination with triphenylphosphine. Ethylene glycol diacetate is also observed. Carbon monoxide, which is added to some of the examples of Fenton, is described by Fenton, at column 2, lines 48–51, as follows: "If desired, a suitable inert gas, such as carbon monoxide can also be charged to the reaction zone—". (Emphasis added). Of particular significance is the fact that none of Fenton's examples produce a methyl ester, as are produced by the process of copending U.S. patent application Ser. No. 971,667, discussed below and encompassed herein. Another point is that Fenton's ethylidene diacetate can be thermally cracked to produce vinyl acetate, see column 1, lines 42–44. It would seem possible that such occurred in Example 1 of Fenton and it is further possible that acetic acid added to the vinyl acetate to form ethylene glycol diacetate.

The following is believed to be a fair analysis of the aforementioned references, i.e., what they teach one skilled in the art and the direction that they could lead one in pursuit of whatever is their objectives:

(1) Gresham, U.S. Pat. No. 2,636,046 states that at exceedingly high pressures in excess of 1,500 atmospheres, that is in excess of about 1,550 kg/cm$^2$, one can produce some glycol and glycol esters by the reaction of carbon monoxide and hydrogen utilizing, most desirably, a cobalt catalyst although some undescribed ruthenium compound can be substituted for cobalt.

(2) The Pruett and Walker patent makes a showing in Examples 9 and 17 at columns 11 and 12, respectively, that the reaction of CO and H$_2$ in the presence of ruthenium carbonyl and cobalt carbonyl complexes operated at about 19,000–25,000 pounds/in$^2$ (1,335.8–1,757.7 kg/cm$^2$) pressure will, in the case of ruthenium, produce no polyhydric alcohols and, in the case of cobalt, produce trace amounts of mono and diacetates of ethylene glycol. Thus, with respect to the cobalt catalyst a minimum pressure of about 19,000 psi (1,335.8 kg/cm$^2$) seems to be needed to make any glycol compound. In the case of ruthenium, the pressure at which glycol can be made from CO and $H_2$ had not been defined.

(3) Howk, et al. (U.S. Pat. No. 2,549,470) who employ a lower pressure reaction than Gresham (U.S. Pat. No. 2,636,046) produce only monohydric alcohols from the reaction of CO and $H_2$ using a solid ruthenium catalyst.* The maximum pressure for the Howk, et al. process is about 1,000 atmospheres. The reaction produces a spectrum of monohydric alcohols ranging from methanol to very high molecular weight alcohols, some alcohols containing up to 40 carbon atoms. The products are classified as pentane soluble materials and pentane insoluble materials. The pentane insoluble higher alcohols are characterized as waxes and less desirable than the pentane soluble alcohols. When Howk, et al. ran the reaction in acetic acid at a pressure ranging from 300 to 950 atmospheres, there was produced "a large quantity of wax together with a liquid." The amount of wax was essentially the same amount, in parts by weight, as ester products, assumed to be esters of monohydric alcohols.

*See Catalysis, supra, who class the Howk, et al. catalytic process as heterogeneous, and Example 83, infra, which supports such classification.

(4) The second Gresham Patent (U.S. Pat. No. 2,535,060) appears to be an improvement on the Howk, et al. patent. It describes the desirability of controlling the pH of the reaction medium in the reaction between carbon monoxide and hydrogen in the presence of a ruthenium-containing catalyst such as described by Howk, et al. The presence of trace amounts of carboxylic acid is considered very undesirable by Gresham. Gresham states that traces of carboxylic acids produce an acidity which "has a very profound effect upon the subsequent course of the reaction, causing the formation of relatively longer chain products, such as waxy alcohols containing up to 50 or more carbon atoms per molecule (c.f. copending application of Hager and Howk, Ser. No. 87,114, filed Apr. 12, 1949). If the pH is more strongly acidic, high molecular weight waxy products are formed in still greater proportions." The copending application referred to is the Howk, et al., U.S. Pat. No. 2,549,470, mentioned previously. Thus, Gresham specifies that it is desirable to maintain the pH of the reaction solution alkaline in order to obtain a better distribution of straight chain monohydric primary alcohols. According to Gresham, the quantity of methanol formed in his reaction "is extremely small" (see column 1, line 49).

(5) There is apparently a minimum pressure according to Howk, et al. used to avoid the formation of hydrocarbons and this appears to be supported by the disclosure of Masters, et al., supra. However, in view of Doyle, et al., supra, there may be a greater similarity in the processes of Howk, et al. and Masters, et al.

(6) The choice of metal catalyst and the appropriate conditions for such kinds of reactions are not predictable. For example, Pruett, et al., the Gresham patents, Howk, et al., and Pruett, state that many metals do not function as catalysts in the reactions they are concerned with.

(7) Fenton utilized rhodium, palladium and ruthenium halides in the presence of a mixture of hydrogen and carbon monoxide and an acid anhydride, and recognized only the reduction of the anhydride.

In copending application Ser. No. 971,667, filed Dec. 21, 1978, of which this application is a continuation-in-part, there is described a process for producing methyl and ethylene glycol esters by reacting carbon monoxide and hydrogen in a homogeneous liquid phase mixture comprising a ruthenium carbonyl complex and acyl compound such as acetic acid. The reaction is effected at a temperature between about 50° C. to about 400° C. and a pressure of between about 500 psia (35.15 kg/cm$^2$) and about 12,500 psia (878.84 kg/cm$^2$) for a period of time sufficient to produce such esters as the predominant product.

In copending application Ser. No. 971,750, filed Dec. 21, 1978, there is described an improved process for producing methyl and ethylene glycol esters as described in Ser. No. 971,667 in which the improvement comprises maintaining the combined concentration of methyl ester, ethylene glycol ester and water in the reaction medium at less than about 30 vol. %.

In a recent publication (J. S. Bradley, Journal of the American Chemical Society, 101, 7419 (1979)), it is reported that methanol and methyl formate could be produced at a selectivity greater than 99% without hydrocarbon products detected, by the reaction of synthesis gas ($H_2$:CO=3.2) under pressures on the order of 1,300 atmospheres and at temperatures around 270° C. using a Ru catalyst, which was present under conditions of the reaction as Ru(CO)$_5$. Bradley observed no ethanol, ethylene glycol, or acetates. Compare this result with that found by Pruett and Walker, supra, and the work of Fonseca, et al and Williamson et al, infra.

An interesting exception to the previously reported inactivity of ruthenium catalyst to produce glycol is the high pressure (via 1650–1750 bars) experiment reported by A. Deluzarche, et al., High Pressure Science And Technology, 6th AIRAPT Conference (Chapt. "High Pressure Synthesis Of Polyalcohols By Catalytic Hydrogenation Of Carbon Monoxide"), pages 733–738 (1979), published by Plenum Press, New York (see also a discussion of the same work in Erdöl Und Kohle, 32, 313 (1979)). The authors report the reaction in tetraglyme of a CO:H$_2$ (1:2 ratio) mixture at 1650–1765 bars, i.e., about 25,000 psi (1,757.6 Kg/cm$^2$) and 230° C. using triruthenium dodecacarbonyl and 2-pyridinol as a ligand, both in unstated amounts, for a period of 5 hours. The authors report a percent conversion of 12.9 (unstated basis), and percent yield of polyols of 3 (unstated basis), and percent selectivities as follows: ethylene glycol, 22.9; glycerine, 0; methanol, 16.1. However, in a manuscript entitled "Reactions CO-H$_2$ in Liquid Phase in Presence of Ruthenium Catalysts" to be published by Jenner, Kiennemann, Bagherzadah, and Deluzarche, et al, it is stated that with respect to the above experiment, "We never could reproduce the run with Ru$_3$(CO)$_{12}$ when operating in a vessel which has not been in contact with any rhodium catalyst. We suspect that in the former run, the formation of ethylene glycol was due to catalysis with metallic sediments of rhodium incrusted on the wall of the vessel (we showed that ethylene glycol is produced in appreciable yield with rhodium foam)".*

*This report casts some doubt on the identity of the catalyst which produces glycol in experiments reported by Williamson et al., (infra) and Keim et al., (infra); these experiments were run under conditions very similar to those employed in the first report by A. Deluzarche, et al.

In Williamson, et al., U.S. Pat. No. 4,170,605 patented Oct. 9, 1979 the patentees report in Examples I and II the reaction in 1-propanol of synthesis gas (CO:H$_2$=1:1) at 25,000 psig and at 230° C. using ruthenium tris(acetylacetonate) and 2-hydroxypyridine, the latter being the same ligand employed by Deluzarche, et al., supra, for a period of 2 and 3 hours, respectively. In Example I, Williamson, et al., report the production of 4 grams of product containing (mole percent basis): ethylene glycol, 57; and methanol 25. In Example II, 7 grams of product are reported containing 66 and 16 mole percent of ethylene glycol and methanol, respectively.

**Included in the 4 and 7 grams of product are trace amounts of water and methylformate as well as 16 mole percent (Example I) and 15 mole percent (Example II) of propylformate. The latter compound would appear to be derived from 1-propanol initially present in the reaction mixture, rather than a synthesis gas-derived product.

W. Keim, et al., (Journal of Catalysis, 61, 359 (1980)) have reported that reactions of Ru$_3$(CO)$_{12}$ under very high pressures (2,000 bars) produce mainly methanol and methyl formate, but traces of glycol (0.8 to 1.2 percent of the total products) were also seen. In one experiment a small amount of ethanol was detected. No glycerine was observed in these reactions.

As pointed out above, ethylene glycol can be produced directly from a mixture of hydrogen and carbon monoxide using a rhodium carbonyl complex as a catalyst. The literature describes (see U.S. Pat. No. 3,957,857, issued May 18, 1976) that a desirable rhodium compound can be in the form of a rhodium carbonyl cluster compound, particularly one which exhibits a particular 3-band infrared spectral pattern. There has been a substantial amount of work done on the formation of ethylene glycol from mixtures of hydrogen and carbon monoxide in the presence of rhodium carbonyl clusters (see the list of patents and applications recited in footnoted Table A below*).

*TABLE A

| | |
|---|---|
| U.S. Pat. No. 3,833,634 | Patented September 3, 1974 |
| U.S. Pat. No. 3,878,214 | Patented April 15, 1975 |
| U.S. Pat. No. 3,878,290 | Patented April 15, 1975 |
| U.S. Pat. No. 3,878,292 | Patented April 15, 1975 |
| U.S. Pat. No. 3,886,364 | Patented May 27, 1975 |
| U.S. Pat. No. 3,929,969 | Patented December 30, 1975 |
| U.S. Pat. No. 3,940,432 | Patented February 24, 1976 |
| U.S. Pat. No. 3,944,588 | Patented March 16, 1976 |
| U.S. Pat. No. 3,948,965 | Patented April 6, 1976 |
| U.S. Pat. No. 3,952,039 | Patented April 20, 1976 |
| U.S. Pat. No. 3,957,857 | Patented May 18, 1976 |
| U.S. Pat. No. 3,968,136 | Patented July 6, 1976 |
| U.S. Pat. No. 3,974,259 | Patented August 10, 1976 |
| U.S. Pat. No. 3,989,799 | Patented November 2, 1976 |
| U.S. Pat. No. 4,001,289 | Patented January 4, 1977 |
| U.S. Pat. No. 4,013,700 | Patented March 22, 1977 |
| U.S. Pat. No. 4,111,975 | Patented September 5, 1978 |
| U.S. Pat. No. 4,115,428 | Patented September 19, 1978 |
| U.S. Pat. No. 4,115,433 | Patented September 19, 1978 |
| U.S. Pat. No. 4,133,776 | Patented January 9, 1979 |
| U.S. Pat. No. 4,151,192 | Patented April 24, 1979 |
| U.S. Pat. No. 4,153,623 | Patented May 8, 1979 |
| U.S. Pat. No. 4,162,261 | Patented July 24, 1979 |
| U.S. Pat. No. 4,191,701 | Patented March 4, 1980 |
| U.S. Pat. No. 4,199,521 | Patented April 22, 1980 |
| U.S. Pat. No. 4,188,335 | Patented February 12, 1980 |
| U.S. Pat. No. 4,199,520 | Patented April 22, 1980 |
| U.S. Pat. No. 4,197,253 | Patented April 8, 1980 |
| U.S. Pat. No. 4,190,598 | Patented February 26, 1980 |
| U.S. Pat. No. 4,180,517 | Patented December 25, 1979 |
| U.S. Pat. No. 4,224,235 | Patented September 23, 1980 |
| U.S. Pat. No. 4,225,530 | Patented September 30, 1980 |
| U.S. Pat. No. 4,211,719 | Patented July 8, 1980 |
| U.S. Pat. No. 4,224,237 | Patented September 23, 1980 |
| U.S. Ser. No. 138,973 | Filed April 10, 1980 |
| U.S. Ser. No. 715,853 | Filed August 19, 1976 |
| U.S. Ser. No. 862,554 | Filed December 20, 1977 |
| U.S. Ser. No. 882,396 | Filed March 1, 1978 |
| U.S. Ser. No. 919,419 | Filed June 27, 1978 |
| U.S. Ser. No. 946,313 | Filed September 27, 1978 |
| U.S. Ser. No. 146,211 | Filed May 5, 1980 |
| U.S. Ser. No. 144,048 | Filed April 28, 1980 |
| U.S. Ser. No. 062,357 | Filed July 31, 1979 |
| U.S. Ser. No. 070,003 | Filed August 27, 1979 |
| U.S. Ser. No. 071,576 | Filed August 31, 1979 |
| U.S. Ser. No. 081,919 | Filed October 4, 1979 |

The above discussion provides a detailed characterization of technology heretofore published or filed upon which relates to the direct production of ethylene glycol from mixtures of carbon monoxide and hydrogen or the production of monohydric alcohols from the direct reaction of hydrogen and carbon monoxide in the presence of a ruthenium catalyst. For the purposes of the discussion and descriptions contained herein, mixtures of hydrogen and carbon monoxide, regardless of the amount of each present, will be characterized, for the sake of convenience, as "synthesis gas". Thus, mole ratios of hydrogen to carbon monoxide of e.g. 40 to 1 and 0.05 to 1 are arbitrarily classified as "synthesis gas". Where the molar ratio of one to the other is significant to the invention herein described, then specific reference to the desired molar ratio will be made.

THE PROBLEM

Owing to the limited availability of petroleum sources the cost of producing chemicals from petroleum has been steadily increasing. Many have raised the dire prediction of significant oil shortages in the future. Obviously a different low cost source is needed which can be converted into the valuable chemicals now derived from petroleum sources. Synthesis gas is one such source which can be effectively utilized in certain circumstances to make chemicals.

The most desirable aspect of synthesis gas is that it can be produced from non-petroleum sources. Synthesis gas is derived by the combustion of any carbonaceous material including coal, or any organic material, such as hydrocarbons, carbohydrates and the like. Synthesis gas has for a long time been considered a desirable starting material for the manufacture of a variety of chemicals. A number of chemicals have been made commercially from synthesis gas. Hydrocarbons have been made by the Fischer-Tropsch catalytic reaction. Methanol is commercially manufactured by a heterogeneous catalytic reaction from synthesis gas. Aldehydes and alcohols are made from the reaction of olefins and synthesis gas. If one could expand the production of chemicals in a commercial manner from synthesis gas then one would not be as presently dependent upon petroleum as the basic raw material even though it is an excellent raw material for making synthesis gas.

There is described herein a process which has wide ranging possibilities for the production of a host of valuable chemicals. The process of this invention involves the conversion of synthesis gas, however derived, into a limited variety of valuable alcohol compounds which themselves can be directly consumed or which can be employed as starting materials to make other valuable chemicals. The process of this invention is concerned with making 2 carbon atom alcohols, to wit, ethanol and ethylene glycol and in particular, ethylene glycol. In addition, the process of this invention also produces large amounts of methanol. The process of this invention is capable of producing predominantly ethylene glycol or predominantly methanol, or predominantly ethanol, or mixtures of them each in large concentrations. The process of this invention provides the capability of a low cost route to methanol, ethanol and ethylene glycol, especially ethylene glycol.

One of the deficiencies of the aforementioned processes for making ethylene glycol from synthesis gas utilizing a rhodium carbonyl complex catalyst is the enormous price of rhodium. Rhodium presently is employed in catalytic converters which comprise the automotive combustion devices for reducing automotive pollutant emissions. The high cost of rhodium is created by its limited availability and the tremendous demand for it. Thus, a commercial process which uses rhodium as a catalyst is affected by the high capital expense to purchase the metal and the strict controls needed to limit catalyst losses in order to keep the economics of the process competitive.* Ruthenium, on the other hand, is a precious metal which has no significant commercial application. Its present cost is approximately 1/20th and less than that of rhodium even though its concentration in the ore from which both are obtained is about the same. Ruthenium has been explored as a catalyst by many. It has been considered as a hydrogenation catalyst, as a hydroformylation catalyst, as a catalyst to produce a wide range of monohydric alcohols (nonspecific as to any of them) exclusive of methanol, as an alcohol homologation catalyst such as for the conversion of methanol to ethanol,** as a high pressure catalyst to selectively produce methanol and methyl formate, and its inactivity has been noted as a catalyst to produce glycol, see above.

*See Cornils, et al., Hydrocarbon Processing, June, 1975, pp. 83 to 91.
**See, for example, U.S. Pat. Nos. 4,133,966 and 3,285,948; and Japanese Patent Application (Kokai) No. 52-73804/77 (June 21, 1977) [Application No. 50-149391/75 (application date, Dec. 15, 1975)] to Mitsubishi Gas Chemical Industry Company.

THE INVENTION

This invention relates to processes and catalysts for selectively making the products methanol, ethylene glycol and ethanol, or derivative precursors such as acylates, directly from the reaction of hydrogen and carbon monoxide. The process comprises:

(a) establishing and maintaining a solvent-containing liquid phase comprising solubilized ruthenium carbonyl complex in which the solvent has a dielectric constant of at least 2, determined at 25° C. or at its melting point, whichever is higher;

(b) supplying hydrogen and carbon monoxide in said liquid phase; and (c) maintaining said liquid phase for a sufficient period of time at a temperature and pressure which causes said hydrogen and carbon monoxide to react to produce such products, said temperature is between about 50° C. and 400° C. and said pressure is between about 500 psia (35.15 kg/cm$^2$) and 15,000 psia (1,054.6 kg/cm$^2$). The catalyst of this invention is that catalyst which is formed during the course of the reaction.

Further details of the invention are recited below.

COMPARISON OF INVENTION WITH CITED ART

The process of this invention is distinguishable from the aforementioned reported work and disclosures of others in the following ways:

(1) As to Gresham, U.S. Pat. No. 2,535,060, supra, the present invention employs a homogeneous liquid phase catalytic reaction in which the catalyst is dissolved in a liquid phase medium, not a heterogeneous reaction as employed by Gresham. In addition, Gresham and Howk et al., supra, produce only straight chain alcohols, offering little selectivity to any of them, and the quantity of methanol formed in Gresham's reaction "is extremely small".

(2) As to Gresham, U.S. Pat. No. 2,636,046, supra, a minimum pressure of 20,580 psi (1,400 atmospheres or 1,446.9 kg/cm$^2$) is required to form polyfunctional oxygen-containing organic compounds as compared with a maximum pressure of about 15,000 psi (1,054.6 kg/cm$^2$) for this invention. Gresham fails to show that ruthenium in any particular form functions as an effective catalyst at even his high pressures. It is believed that Gresham's high pressure requirements make his process commercially uneconomical, particularly when considered in the light of the amount of glycol produced with his preferred cobalt catalyst (see Pruett and Walker, supra, Example 17).

(3) Pruett, supra, and Pruett, et al., supra, establish the view that ruthenium carbonyl complexes would not function to produce ethylene glycol, even at extremely high pressures, viz. 1,300–1,700 atmospheres [19,110 psi (1,343.57 kg/cm$^2$)-24,990 psi (1,757 kg/cm$^2$)]. This is supported by Bradley, supra, who effected the reaction at 1,300 atmospheres and obtained no ethylene glycol.

(4) A. Deluzarche, et al., supra, Williamson, et al., supra, and Keim, et al., supra which are the only art citations which produced any ethylene glycol using a ruthenium-containing catalyst, performed their experiments at extreme pressures of about 25,000 psi or greater. There is little certainty, as stated above, that a ruthenium complex is the actual catalyst which produced the ethylene glycol observed under these extreme conditions. Neither Deluzarche, et al., nor Williamson, et al., report the formation of ethanol or glycerine at 25,000 psi. The instant process, on the other hand, is effected at pressures below 15,000 psi and, in addition to providing ethylene glycol at such substantially lower pressures, provides ethanol as well as glycerine.

FURTHER DISCUSSION OF THE INVENTION

This process constitutes a relatively low pressure process for selectively converting synthesis gas to such valuable chemicals as ethylene glycol, ethanol and methanol. Also produced by the process of this invention are glycerol (i.e. glycerine), 1,2-propylene glycol, 1-propanol and methyl formate. However, the process of this invention is mainly concerned with the production of ethylene glycol (the most valued product), ethanol and methanol since they are produced in significantly greater amounts than the other products. This process is capable of being oriented to enhance the selectivity in favor of any one of methanol, ethanol and ethylene glycol. An added feature of this invention is the ability to enhance the productivity, when desired, of such by-products as glycerol. The process of this invention is accomplished even when the predominant products of the reaction are derivatives such as methyl carboxylates, ethyl carboxylates and ethylene glycol mono- and dicarboxylates.

The process of this invention is carried out with the ruthenium carbonyl complex dissolved in a solvent, even though such complex may exist during the reaction in more than one liquid phase. In this sense, the reaction is termed a homogeneous liquid phase reaction.

There may be more than one such phase existing in the reaction zone but the ruthenium carbonyl complex existing as the catalyst is always dissolved in at least one of such phases and is always in a dissolved liquid state. The problem with heterogeneous ruthenium catalysis in the reaction zone is that such will induce the Fischer-Tropsch reaction resulting in the formation of hydrocarbons and/or a variety of oxygenated hydrocarbons having a variety of molecular weights with low selectivity to any one compound. In fact the presence of such products suggests that undissolved ruthenium is present.

The process of this invention involves the solubilization of ruthenium in the presence of synthesis gas at temperatures, pressures and for a period of time sufficient to produce ethylene glycol. Such conditions are set forth herein. In simplistic and in the broadest terms, the invention comprises the solubilization under the reaction conditions (i.e., time, temperature and pressure) of a ruthenium source, preferably ruthenium in the absence of any other platinum group metal (viz., platinum, palladium, rhodium and iridium),* in an appropriate solvent, preferably one which has a dielectric constant of at least 2 determined at 25° C. or at its melting point, whichever is the higher value, under a prescribed synthesis gas pressure. The reaction conditions comprise (i) a period of time at a temperature and pressure which cause the hydrogen and carbon monoxide to react to produce the desired products, (ii) a temperature between about 50° C. and 400° C. and (iii) a pressure between 500 psia (35.15 kg/cm$^2$) and 15,000 psia (1,054.6 kg/cm$^2$). The catalyst of this invention is the ruthenium containing carbonyl complex which under the prescribed reaction conditions catalyzes the aforementioned reaction between carbon monoxide and hydrogen.

*See U.S. Pat. No. 3,989,799, patented Nov. 2, 1976, wherein ruthenium is a cation in a mixed metal rhodium-containing carbonyl complex.

The process of this invention is distinctive in the selection of materials which comprise the homogeneous liquid phase mixture, the reaction parameters and the stability of the ruthenium containing catalyst in most cases, indeed, in all cases studied. As with any technology, this process has undergone evolutionary changes and its further examination will undoubtedly bring about more changes, most likely in the form of additional or substitutional steps and/or materials.

In the preferred form of the invention the process is carried out in the presence of a promoter. A promoter, in the context of this invention, is a material provided to the reaction which provides a promotional effect in that it enhances the production (viz., rate, yield or efficiency) of any of the products, or it improves the selectivity of the reaction toward ethylene glycol rather than methanol or ethanol, or it improves the selectivity of the reaction to ethanol rather than methanol irrespective of the amount of ethylene glycol produced, or it helps to reduce the loss of ruthenium during the reaction. A promoter may be any Lewis base containing compound. Any Lewis base may be a promoter but all Lewis bases will not serve to act as a promoter under any given set of reaction conditions. The effectiveness of the Lewis base as a promoter will in large measure be dependent upon the reaction conditions selected. Operation of the process in the absence of the Lewis base promoter will result in most instances in less productivity and therefore, exploitation of the process in a commercial sense will probably necessitate the use of a promoter.

The amount of Lewis base promoter added to the process is that amount which provides the promotional effect. The maximum amount employed is that amount whose presence is too costly for the economical operation of the process, or substantially reduces the promotional effect without any advantage, or provides no advantage in the operation of the process, or a combination of these factors. The promoter can be a material used in miniscule quantities to a material employed in maximum quantities such as a solvent for the reaction and the ruthenium carbonyl complex catalyst. Indeed, the promoter can be a material such as carboxylic acids, which when present react with the products of the reaction.

Apart from the conditions of the reaction in terms of time, temperature and pressure, the selection of solvent and optionally the Lewis base promoter constitute important considerations in the most advantageous practice of this invention. The selections of solvent and the promoter are not narrowly limited yet there appears to be some degree of cooperation that each imparts to the success of the process and the selection of one oftentimes dictates the selection of the other in order to maximize the benefits of the invention.

It is found necessary that there be used a solvent that is capable of maintaining the chosen ruthenium carbonyl complex and, optionally the Lewis base promoter (if it is not the solvent), in the homogeneous liquid phase mixture throughout the reaction. This appears to be the prime function of the solvent. The solvent may possibly provide an additional benefit such as influencing the kinds of ion pairing that exist during the course of the reaction.

The catalyst of this invention is a ruthenium compound which contains carbon monoxide directly bonded to ruthenium (ruthenium carbonyl). The ruthenium compound which is provided to the reaction is not necessarily in a form which will effectively catalyze the reaction even if it contains a carbon monoxide ligand bonded to it. Ruthenium compounds such as ruthenium salts, oxides and carbonyl clusters may be introduced to the reaction in a condition which allows them to be solubilized, and under the conditions of the reaction they are converted into a carbonyl complex which effectively catalyzes the reaction. That is why they are defined in terms of products made by the process. The composition and structure of the ruthenium carbonyl complex which catalyzes the desired reaction is not specifically known. It may be a monoruthenium or polyruthenium compound. Illustrative of polyruthenium compounds are the well-known cluster compounds of ruthenium. However, the addition of a cluster containing only a carbonyl ligand such as Ru$_3$(CO)$_{12}$ does not alone create the catalyst and as such cause the catalytic reaction. Some modification of such structure is needed, possibly the destruction of the cluster structure to a mononuclear ruthenium structure. Factors in achieving the catalyst are the reaction parameters, the choice of solvent and, optionally, the Lewis base promoter that one employs. Because varied reaction conditions and solvents, with and without promoters, result in different amounts of the desired products of the process, and different rates, efficiencies and/or yields, it is presumed that each provides a different and distinct catalytic environment.

The ruthenium-containing substances which may be employed in the practice of this invention to form the catalyst under process conditions encompass those which are described, for example, in Gresham, U.S. Pat. No. 2,535,060 at column 2, starting at line 38 to line 48, and ruthenium carbonyl compounds. It is not advisable to place ruthenium compounds or substances on a support material for use in the process of this invention because such offers no benefits over solubilizing such ruthenium compounds in combination with the aforementioned solvent and Lewis base promoter. Moreover, ruthenium deposited on a support material can be expected to be solubilized in the homogeneous liquid phase reaction system of this invention as it is contacted with carbon monoxide. Even ruthenium metal in the presence of the solvent, carbon monoxide and hydrogen can be converted to a ruthenium carbonyl complex which is soluble. Ruthenium oxides, such as dioxide, sesquioxide, or tetraoxide, are capable under appropriate conditions of being solubilized and converted to a carbonyl complex which can be used to form the catalyst under the conditions of this process. However, when using such insoluble ruthenium compounds, they must first be solubilized before the effective operation of the process of this invention. Ruthenium carbonyl compounds (which include ruthenium carbonyl hydrides or ruthenium carbonyl clusters) are already provided with a carbonyl ligand, and under the conditions of the reaction can be sufficiently changed to achieve the desired catalytic effect. Ruthenium salts such as those of organic acids can be employed in the practice of this invention to produce the catalyst. In addition to those ruthenium compounds described in the aforementioned Gresham patent, one may employ ruthenium compounds of bidentate ligands, allyl complexes, arene complexes, halides, and alkyl complexes. The choice of ruthenium compounds is varied and not critical to this invention. A number of ruthenium complexes are known to be more stable to the presence of carbon monoxide than other ruthenium compounds and the skilled worker can determine which particular ruthenium compound might take longer to initiate a reaction than other ruthenium compounds. On that basis, one can select for the purposes of convenience the particular ruthenium compound to be utilized in forming the catalyst. However, ruthenium which is associated with an organic molecule or complexed with carbon monoxide is most readily solubilized so as to provide the ruthenium catalyst of this process.

As characterized above, this process is operated as a homogeneous liquid phase mixture. The process is typically carried out in a solvent for the catalyst and the Lewis base promoter, when added. Thus the solvent is a liquid in which the catalyst (presumed to be a ruthenium carbonyl complex) and the added Lewis base promoter are soluble under the prescribed conditions of the reaction. The solvent may be solid at room temperature but should at least in part be a liquid under the conditions of reaction.

A preferred solvent is a liquid at reaction conditions which is polar or complexes ions. Of the polar solvents those which have a relatively high dielectric constant are more preferred. As for the solvents which complex ions, the desirable solvents are those which under the reaction conditions have the capacity of complexing ions such as available cations. As stated previously, the solvent may provide the Lewis base component. Solvents having a dielectric constant at 25° C. or at its melting temperature, whichever is higher, of greater than 2 are preferred.

Illustrative of suitable polar solvents are, e.g., water, ketones, esters including lactones, amides including lactams, sulfones, sulfoxides, halogenated hydrocarbons, aromatic hydrocarbons, and the like. Illustrative of specific solvents encompassed by the above classes of polar solvents are, for example, aromatic hydrocarbons, e.g., benzene, toluene, xylene, naphthalene, alkylnaphthalene, etc.; carboxylic acids such as acetic acid, propionic acid, butyric acid, caproic acid, stearic acid, benzoic acid, cyclohexane-carboxylic acid, etc., see the description of acyl compounds in Ser. No. 971,667; ketones such as acetone, methyl ethyl ketone, cyclohexanone, cyclopentanone, etc.; esters such as methyl acetate, ethyl acetate, propyl acetate, butyl acetate, methyl propionate, ethyl butyrate, methyl laurate, etc.; anhydrides such as phthalic anhydride, acetic anhydride, etc.; lactams such as N-alkyl caprolactam, such as N-methylcaprolactam, N-alkyl pyrrolidinones such as N-methyl pyrrolidinone; cyclic ureas such as N,N'-dimethylimidazolidone; polyols such as ethylene glycol, glycerine, erythritol, polyalkylene glycol containing two to about ten thousand repeating units; lactones such as gamma-butyrolactone; halogenated hydrocarbons such as chlorobenzene, chloroform, methylene chloride, 2,2-dichloropropane; amides such as dimethylformamide, dimethylacetamide, hexamethylphosphoramide; sulfones such as sulfolane, dimethylsulfone, the substituted sulfolanes described in U.S. application Ser. No. 61,456, filed July 27, 1979; sulfoxides such as dimethylsulfoxide, diphenyl sulfoxide; as well as many others.

Illustrative of suitable complexing solvents are the ethers, cryptands, and the like. Illustrative of specific solvents encompassed by the above classes of complexing solvents are, for example, ethers such as tetrahydrofuran, tetrahydropyran, diethyl ether, 1,2-dimethoxybenzene, 1,2-diethoxybenzene, the mono and dialkyl ethers of alkylene and polyalkylene glycols, such as ethylene glycol, of 1,2-propylene glycol, of 1,2-butylene glycol, of diethylene glycol, of di-1,2-propylene glycol, of triethylene glycol, of pentaethylene glycol (such as triglyme, tetraglyme and pentaglyme), of di-1,2-butylene glycol, of oxyethylene-oxypropylene glycols, etc., preferably those in which the alkylene group contains 2 and/or 3 carbon atoms in the divalent moiety, such as ethylene and 1,2-propylene; the cryptands such as described in U.S. Pat. No. 4,111,975, which description of cryptands, as promoters in that case, are incorporated herein by reference; the crown ethers (or Crown Ethers, as one may prefer) such as described in U.S. Pat. No. 4,162,261, which description of crown ethers, as solvents in that case, are incorporated herein by reference; as well as many others.

The choice of solvent in any particular case can be a complex decision. Some solvents such as the carboxylic acids (e.g., acyl compounds described in U.S. patent application Ser. No. 971,667, the disclosure of which is common to the disclosure herein) play a dual role in the practice of the process of this invention. They can provide the required Lewis base promoter as well as the solvent. Other solvents which can play this dual function include, e.g., the crown ethers and the cryptands, as well as many others. In many instances, solvents react with the products of the reaction and such reactive solvents are considered useful in the practice of this invention because the derivative products obtained are an excellent source for the desired products of the reaction. For example, the carboxylic acids are not only effective solvents and promoters, they are also reactive with ethylene glycol, methanol and ethanol products, to produce ethylene glycol dicarboxylates, methyl carboxylates, and ethyl carboxylates. These carboxylates can be readily hydrolyzed to produce the alcohol products. This is not necessarily an uneconomical method to produce such products (for example, Halcon International Inc., New York, N.Y., had planned to produce ethylene glycol commercially by the reaction of acetic acid and ethylene and the hydrolysis of the resulting ethylene diacetate). In many cases (and possibly in the preferred cases) another Lewis base promoter will be employed in combination with a solvent which has the capacity to serve in such dual function. This is because such other Lewis base promoter is found to be more effective in generating the desired products when used in combination with that solvent under the conditions of reaction chosen.

An important class of solvents contemplated in the practice of this invention are mixtures of the aforementioned polar solvents and the complexing solvents. Various polar solvents mixed with other polar or complexing solvents are contemplated to provide enhanced results either in terms of rates, selectivity, conversions and/or yields of one or more of the desired products. Which mixtures will achieve what result has hot been determined. Combinations of, e.g., sulfolane with crown ethers, lactones, amides or ureas are contemplated as potentially useful. Combinations of, e.g., crown ethers with lactones, amides, and ureas are contemplated as potentially useful.

The Lewis bases suitable as promoters in the practice of this process are not a narrowly defined class of materials. They encompass a broad range of inorganic and organic materials, and all members of the class are contemplated as employable in the practice of this invention. Its effectiveness in some instances can be noted when used in as little an amount which is the least amount that a measurable promotional effect is seen to an amount wherein the Lewis base is also a solvent for the reaction. The Lewis base can serve a dual function by playing the role as the solvent for the reaction. There is no simple way of determining what Lewis base will function effectively under a given set of reaction conditions. In the typical case, when a Lewis base exhibits promotional affects on the rate of the reaction, it is present and dissolved in the liquid phase in a range of from about 0.01 mole to about $10^6$ moles for each atom (gram atomic weight) of ruthenium present in the reaction. More preferred, the Lewis base is present (even when the solvent used is a Lewis base) in the liquid phase in a range from about 1 mole to about $10^4$ moles for each atom of ruthenium present in the reaction; most preferably, greater than one mole up to about 1000 moles of the Lewis base for each atom of ruthenium present and dissolved in the liquid phase.

The Lewis base promoters include inorganic as well as organic compounds. Illustrative of suitable organic compounds are those containing at least one Lewis base nitrogen atom or at least one Lewis base oxygen atom or a combination of such nitrogen and oxygen atoms. The carbon atoms can be part of an acyclic and/or cyclic radical such as aliphatic, cycloaliphatic and aromatic carbon radicals. Usually, the organic Lewis bases contain at least 2 carbon atoms and no more than 40 carbon atoms. The Lewis base nitrogen atoms are usually in the form of imino (—N=), amino (—N—) and nitrilo (N≡), etc. The Lewis base oxygen atoms can be in the form of groups such as hydroxyl (aliphatic or phenolic), carboxyl

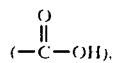

carbonyloxy

oxy (—O—), carbonyl

etc. The organic Lewis bases may also contain other atoms and/or groups as substituents of the aforementioned radicals such as alkyl, aryl and chloro substituents. The Lewis base promoter also includes a variety of inorganic compounds such as, for example, inorganic amines and a variety of inorganic metal compounds.

Illustrative of suitable classes of Lewis base promoters are, for example, any of the following: monoamines and polyamines including those compounds in which Lewis base nitrogen forms part of a ring structure; alkanolamines; acyl compounds including aliphatic, cycloaliphatic and aromatic carboxylic acids, ester derivatives and anhydrides of such acids, usually having no more than 20 carbon atoms; bis(triorgano phosphine)iminium compounds; ketones; ethers; amides; crown ethers; cryptands; hydroxides and salts of various metals including, for example, carboxylates, halides, carbonates, bicarbonates, sulfates and bisulfates of any of the alkali metals, alkaline earth metals as well as of other metals such as iron; as well as many other compounds which can function as Lewis bases or serve as a source for the Lewis base under reaction conditions.

Illustrative of specific Lewis bases are the following:
Methyl-, ethyl-, isopropyl- and octylamines
Dimethyl-, diisoamyl- and diisobutylamines
Methylethylamine
Trimethyl- and triethylamines
Methyldiethylamine
Triisobutyl- and tridecylamines
1,2-Ethanediamine
1,3-Propanediamine
Diethylenetriamine
Triethylenetetraamine
Tetraethylenepentaamine,
    NH$_2$CH$_2$CH$_2$NHCH$_2$CH$_2$NHCH$_2$CH$_2$NHCH$_2$CH$_2$NH$_2$
N,N,N',N'-Tetramethylethylenediamine,
    (CH$_3$)$_2$NCH$_2$CH$_2$N(CH$_3$)$_2$
N-Pentamethyldiethylenetriamine
p-Phenylenediamine
o-Tolidene
Aniline
1-Naphthyl- and 2-naphthylamines
p-Toluidine
Benzylamine
Diphenylamine
Dimethylaniline Bis-(1,8)-dimethylaminonaphthalene
Cyclohexylamine
Dicyclohexylamine
Piperidine and N-methylpiperidine
3-Phenylpiperidine
Pyridine and 2-methylpyridine
2,4,6-Trimethylpyridine
2-Dodecylpyridine
2-Aminopyridine
2-(Dimethylamino)pyridine
Quinoline
2-(Dimethylamino)-6-methoxyqinoline
Pyrimidine
1,8-Phenanthroline
Piperazine
N-methyl- and N-ethylpiperazines
2,2'-Bipyridyl and alkyl-substituted 2,2'-bipyridyls
1,4-Diazabicyclo[2.2.2]octane ("triethylenediamine")
Hexamethylenetetraamine
Purine
Isopropanolamine
Diethanolamine
Di-n-propanolamine
Triethanolamine
Triisopropanolamine
Bis(dimethylaminoethyl)ether
N,N-dimethylglycine
N-methyliminodiacetic acid
2-Hydroxypyridine
2-Methoxypyridine
2,6-Dimethoxypyridine
4-Methyl-2-hydroxypyridine
4-Methyl-2,6-dihydroxypyridine
Morpholine
N-methyl- and N-ethylmorpholines
Hexadecylmorpholine
Ethylenedimorpholine
Tetraethylenedimorpholine
Picolinic acid
Nitrilotriacetic acid
2,5-Dicarboxypiperazine
N-(2-hydroxyethyl)-iminodiacetic acid
2,6-Dicarboxypyridine
Ammonia
Hydroxylamine
Hydrazine
Hexamethylphosphoramide
Dimethylformamide
N-Methylpyrrolidinone
Acetic acid
Propionic acid
Butyric acid
2,2,6,6-Tetramethylheptane-3,5-dione, $(CH_3)_3CC(O)CH_2C(O)C(CH_3)_3$
Sulfolane
18-Crown-6
15-Crown-5
Tetrahydrofuran
Diphenylether
Bis(triphenylphosphine)iminium chloride, $[(C_6H_5)_3P]_2N^+Cl^-$
Bis(triphenylphosphine)iminium iodide, $[(C_6H_5)_3P]_2N^+I^-$
Cesium formate
Sodium acetate
Sodium sulfate
Potassium carbonate
Potassium bicarbonate
Cesium oxide
Cesium hydroxide
Potassium hydroxide
Magnesium bromide
Calcium iodide
Cesium bromide
Sodium fluoride
Potassium fluoride
Rubidium bromide
Cesium iodide
Rubidium iodide
Potassium iodide
Sodium iodide
Sodium bromide
Lithium iodide
Lithium bromide
Lithium chloride
Potassium chloride
Lithium diethylamide
Sodium phenyl
Butyllithium
Cobalt diiodide, e.g. $CoI_2.2H_2O$
Tetracarbonyl cobaltate anion, $[Co(CO)_4]^{-1}$
Ferrous iodide, e.g. $FeI_2.4H_2O$ Not all of the above Lewis bases, or for that matter all Lewis bases, will necessarily function effectively in all of the embodiments of the process of this invention. In most cases a degree of selection between the choice of Lewis base, the amount of ruthenium, the choice of solvent and the reaction parameters will be required to obtain the level of productivity sought.

Because $H_2$ is supplied to the reaction, a hydride of ruthenium can exist in the reaction system. There is no appreciation of the particular role that hydride is playing in the reaction. It is believed that either too much or too little hydrogen present in the reaction will not favor the production of ethylene glycol. In such a case, one can contemplate a role for hydride in the reaction mechanisms occurring.

Though the process of this invention is capable of providing a combination of ethylene glycol, ethanol and methanol, in many instances one or more of them is formed as a minor component only. Because ethylene glycol is the most valued of the products, its production obviously makes this process attractive. By the same reasoning, ethanol's higher market value than methanol also enhances the commercial attractiveness of this process. A process which produces the same amount of ethylene glycol and produces more ethanol will have more commercial attractiveness, assuming all other factors are equal.

At this time, no particular basis has been found for predicting whether any particular set of process conditions and reactants encompassed by this invention will produce ethanol except those that have already been established by experimentation. It has been found that certain process conditions do produce ethanol while others are not apparently as effective in producing ethanol. The ability to make ethanol may reside in the particular ruthenium catalyst, the Lewis base promoter (if employed), the solvent, and/or the temperature and pressure of reaction, but in all probability ethanol production is dependent on a combination of all of these.

The relative amounts of carbon monoxide and hydrogen which are initially present in the reaction mixture can be varied over a wide range. In general, the molar ratio of $CO:H_2$ is in the range of from about 40:1 to about 1:40, suitably from about 20:1 to about 1:20, and preferably from about 10:1 to about 1:10. It is to be understood, however, that molar ratios outside the broadest of these ranges may be employed. Substances or reaction mixtures which give rise to the formation of carbon monoxide and hydrogen under the reaction conditions may be employed instead of mixtures comprising carbon monoxide and hydrogen which are used in preferred embodiments in the practice of the invention. For instance, the product alcohols are contemplated as obtainable by using mixtures containing carbon dioxide and hydrogen. Mixtures of carbon dioxide, carbon monoxide and hydrogen can also be employed. If desired, the reaction mixture can comprise steam and carbon monoxide.

The quantity of catalyst employed is not narrowly critical and can vary over a wide range. In general, the process is desirably conducted in the presence of a catalytically effective quantity of the active ruthenium species which gives a suitable and reasonable reaction rate. Reaction can proceed when employing as little as about $1 \times 10^{-6}$ weight percent, and even lesser amounts, of ruthenium based on the total weight of reaction mixture (i.e., the liquid phase mixture). The upper concentration limit can be quite high, e.g., about 30 weight percent ruthenium, and higher, and the realistic upper limit in practicing the invention appears to be dictated and controlled by economics in view of the cost of ruthenium. Since the rate of conversion of synthesis gas may be dependent upon the concentration of ruthenium employed, higher concentrations achieving higher rates, then large concentrations may prove to be a most desirable embodiment of this invention. Depending on various factors such as the Lewis base promoter (if employed), the partial pressures of carbon monoxide and hydrogen, the total operative pressure of the system, the operative temperature, the choice of solvent, and other considerations, a catalyst concentration of from about $1 \times 10^{-3}$ to about 20 weight percent ruthenium (contained in the complex catalyst) based on the total weight of reaction mixture, is generally desirable in the practice of the invention.

The temperature which may be employed in practicing the process may vary over a wide range of elevated temperatures. In general, the process can be conducted at a temperature between about 50° C. and about 400° C. and higher. Temperatures outside this stated range, though not excluded from the scope of the invention, do not fall within certain desirable embodiments of the invention. At the lower end of the temperature range, and lower, the rate of reaction to desired product becomes markedly slow. At the upper temperature range, and beyond, catalyst, solvent, or Lewis base promoter instability may occur. Notwithstanding these factors, reaction will continue and the alcohols and/or their derivatives will be produced. Additionally, one should take notice of the equilibrium reaction for forming ethylene glycol:

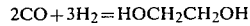

$$2CO + 3H_2 = HOCH_2CH_2OH$$

At relatively high temperatures the equilibrium increasingly favors the left hand side of the equation. To drive the reaction to the formation of increased quantities of ethylene glycol, higher partial pressures of carbon monoxide and hydrogen are required. Processes based on correspondingly higher operative pressures, however, do not represent preferred embodiments of the invention in view of the high investment costs associated with erecting chemical plants which utilize high pressure utilities and the necessity of fabricating equipment capable of withstanding such enormous pressures. Preferred temperatures are between about 100° C. and about 350° C., and most desirably between about 150° C. and about 300° C.

The process is suitably effected over a wide superatmospheric pressure range. At pressures in the direction of and below about 500 psia (35.15 kg/cm²) the rate of desired product formation is quite slow, and consequently, relatively faster reaction rates and/or higher conversions to the desired products can be obtained by employing higher pressures, e.g., pressures of at least about 1,000 psia (70.31 kg/cm²). Pressures as high as 20,000 to 50,000 psia (3,515.35 kg/cm²), and higher, can be employed but there is no apparent advantage in using such pressures, and any advantage that could be reasonably contemplated would be easily offset by the very unattractive plant investment outlay required for such high pressure equipment and the costs associated with such high pressure operations. Therefore, the upper pressure limitation is approximately 15,000 psia (1,054.6 kg/cm²). Effecting the process below about 15,000 psia (1,054.6 kg/cm²), especially below about 10,000 psia (703.1 kg/cm²), results in significant cost advantages which are associated with lower pressure equipment requirements and operating costs. A suitable pressure range is from about 500 psia (35.15 kg/cm²) to about 12,500 psia (878.84 kg/cm²). The pressures referred to above represent the total pressure of hydrogen and carbon monoxide.

The process is effected for a period of time sufficient to produce the desired alcohol products and/or derivatives thereof. In general, the residence time to produce the desired products can vary from minutes to a number of hours, e.g., from a few minutes to 24 hours, and longer. It is readily appreciated that the residence period (time) will be influenced to a significant extent by the reaction temperature, the concentration and choice of Lewis base promoter and ruthenium source, the total gas pressure and the partial pressure exerted by its components, the concentration and choice of solvent, and other factors. The synthesis of the desired product(s) by the reaction of hydrogen with carbon monoxide is suitably conducted under operative conditions which give reasonable reaction rates and/or conversions.

The process can be executed in a batch, semi-continuous, or continuous fashion. The reaction can be conducted in a single reaction zone or a plurality of reaction zones, in series or in parallel, or it may be conducted intermittently or continuously in an elongated tubular zone or series of such zones. The material of construction should be such that it is inert during the reaction and the fabrication of the equipment should be able to withstand the reaction temperature and pressure. The reaction zone can be fitted with internal and/or external heat exchanger(s) to thus control undue temperature fluctuations, or to prevent any possible "runaway" reaction temperature due to the exothermic nature of the reaction. In preferred embodiments of the invention, agitation means to vary the degree of mixing of the reaction mixture can be suitably employed. Mixing induced by vibration, shaker, stirrer, rotatory, oscillation, ultrasonic, etc., are all illustrative of the types of agitation means which are contemplated. Such means are available and well-known to the art. The catalyst precursor may be initially introduced into the reaction zone batchwise, or it may be continuously or intermittently introduced into such zone during the course of the synthesis reaction. Means to introduce and/or adjust the reactants, either intermittently or continuously, into the reaction zone during the course of the reaction can be conveniently utilized in the process especially to maintain the desired molar ratios of, and the partial pressures exerted by, the reactants.

As intimated previously, the operative conditions can be adjusted to optimize the conversion of the desired product and/or the economics of the process. In a continuous process, for instance, when it is preferred to operate at relatively low conversions, it is generally desirable to recirculate unreacted synthesis gas with/without make-up carbon monoxide and hydrogen to the reactor. Recovery of the desired product can be achieved by methods well-known in the art such as by distillation, fractionation, extraction, and the like. A fraction comprising ruthenium complex, generally contained in byproducts and/or the solvent, can be recycled to the reaction zone, if desired. All or a portion of such fraction can be removed for recovery of the ruthenium values or regeneration thereof, if necessary. Fresh ruthenium precursor, Lewis base promoter and/or solvent, can be intermittently added to the recycle stream or directly to the reaction zone, if needed.

Many embodiments of the ruthenium carbonyl complex, Lewis base promoter and solvent combinations encompassed by this invention are sufficiently stable to allow repeated use of the ruthenium carbonyl complex. This is especially noted when the promoter is an alkali metal halide, particularly and preferably an alkali metal iodide. For example, the process of this invention can be continuously operated in a pressure reactor into which is continuously fed synthesis gas. The velocity of the synthesis gas is sufficient to strip products of the reaction out of the reactor leaving behind in the reactor the ruthenium carbonyl complex, Lewis base and solvent combination. The products are separated from the unreacted synthesis gas and the synthesis gas is recycled to the reactor. The products, in this embodiment, are recovered free of ruthenium, Lewis base and solvent. In this embodiment, the catalyst need not be removed from the reactor to a recovery zone for separating product. Thus a catalyst treatment step is avoided. The examples below depict batch reactions; however, the above continuous gas recycle process can be operated in a similar manner as described below. That is, the batch reactor simulates the continuous reactor except for the gas sparging and continuous gas recycle.

In order to describe the continuous process of this invention with particularity, reference is made, for purposes of illustration only, to the accompanying drawing which depicts a schematic flowsheet of a continuous operating unit for practice of this invention.

Referring to the drawing, reactor 1 is a back-mixed stirred reactor surrounded by cooling jacket 3 through which flows a heat transfer fluid for the purpose of maintaining temperature control. The temperature of reactor 1 is typically between 200° and 250° C. A stirrer 5 is contained within reactor 1 for the purpose of maintaining uniform distribution of product and solution in the reactor during the course of the reaction. The reactor 1 is fabricated from 316 stainless steel and is capable of withstanding pressures of up to 30,000 psi. A liquid recycle stream and synthesis gas are supplied to the reactor 1 through line 19. A carbon monoxide feed stream 6 and hydrogen stream 7 are mixed in the desired ratio using a metering system (not shown) which allows the composition of the gas to vary from pure $H_2$ to pure CO. The resultant gas feed is passed through compressor 9 to produce in line 11 a synthesis gas stream at the desired reaction pressure. This gas stream in line 11 is combined with a liquid recycle stream of solvent from line 13 and introduced via line 15 into a pre-heater 17 to heat the mixture of solvent recycle and synthesis gas in line 15 to a temperature very close to the reaction temperature utilized within reactor 1. Methanol, or ethanol, is supplied to the heated feed stream through line 16 in the concentration desired for the purpose of suppressing alcohol formation; the process for suppressing methanol or ethanol formation by providing the alcohol to the reaction is described in copending application Ser. No. 219,873, filed Dec. 24, 1980, now abandoned. These fluid and synthetic gas feed compositions are fed into the reactor through line 19.

The effluent stream from the reactor, which is a mixture of gas and liquid containing the products of the reaction, unreacted synthesis gas, and solvent, passes through line 21 to cooler 23 where the stream temperature is reduced to about 100°–150° C. and thereafter passes through line 25 to pressure reducing valve 27 which reduces the pressure of the effluent entering hold tank 28 to about 10% of the reaction pressure. Hold tank 28 which contains stainless steel packing rings to enhance gas-liquid contact serves to resolubilize volatilized ruthenium complex compounds into the liquid stream. The effluent of tank 28 enters separator 29 wherein substantial amounts of the liquid product and solvent are separated from the effluent stream, the resultant liquid being collected at the bottom of the separator. A portion of the unconverted reactant gas dissolved in the liquid product comes out of solution at the reduced pressure of the separator 29. From the top of separator 29, through line 32, there is removed a stream of essentially gaseous material comprising some methanol and other low boiling components as well as a significant part of the synthesis gas contained in the effluent stream of line 25. The gas stream in line 32 is passed through a throttle valve 31 which controls the pressure in separator 29 and is thereafter fed to low pressure separator 37. The liquid level in the separator 29 is controlled by valve 35 in line 33. High pressure separator 29, typically, is operated at a pressure which is approximately 10% of that contained within reactor 1, whereas low pressure separator 37 is operated at about atmospheric pressure or somewhat above atmospheric pressure. Generally, low pressure separator 37 is operated at as low a pressure as possible, taking into consideration the desire to transport the liquid streams fed therein to stripper 53.

The liquid stream which exits from the bottom of high pressure separator 29 is carried via line 33 through throttle valve 35 to low pressure separator 37, the liquid being collected at the bottom of separator 37. The gases vented from low pressure separator 37 are taken by way of line 39 into heat exchanger 45 to reduce the temperature of the stream, the condensed liquid product being collected in receiver 47. This liquid product is primarily methanol which can optionally be recycled to reactor 1 by providing a line connecting line 51 to line 16. Synthesis gas and uncondensed products are removed from receiver 47 through line 49 and pressure control valve 52, and pass through a chilled methanol or ethanol scrubber 48 to recover the volatilized ruthenium compounds contained in such stream prior to being vented to the atmosphere. Typically, such vented gases are predominantly the noncondensable gases as well as very small amounts of methanol, ethanol and methyl formate.

The liquid collected in separator 37 is withdrawn through line 41 and throttle valve 43 and enters the upper portion of gas stripper 53. Stripper 53 is surrounded by steam jacket 55 and contains a stainless steel wire mesh packing of the type which creates a very low pressure drop within the column. The liquid product leaving separator 37 is stripped in stripper 53 with synthesis gas which is circulated through stripper 53 in a continuous gas recycle loop, makeup quantities of gas being provided through line 70. The synthesis gas is fed into the lower end of the stripper 53 through line 59 after having been heated in heat exchanger 58 and countercurrently strips the more volatile products contained in the liquid stream entering the stripper through line 41. Stripping gas and vapor products are removed from the overhead of the stripper 53 through line 57 and cooled in condenser 61. Stripping gas and condensed liquid products pass into receiver 63. The liquid products collected in receiver 63 are predominantly methanol, ethanol and ethylene glycol, which are separated from one another by simple distillation. The stripping gas and a small amount of vapor products in receiver 63 are withdrawn through line 69 to recycle compressor 71 and are then passed to stripper 53 to complete the continuous gas loop.

The stripped liquid recovered from the bottom of stripper 53 via line 67 is carried to a collection tank 73 from which it is fed via line 75 into solvent pump 77 for recycling to reactor 1 through line 13 after being admixed with the synthesis gas in line 11 as previously described.

In the preferred embodiment of this invention, the process is operated in a continuous mode by continuously feeding synthesis gas into the liquid phase located within the reaction zone. The selection of solvent is as described above. In the preferred embodiment the Lewis base promoter is also provided to the reaction. A desirable and preferred procedure of operating in this continuous mode is to repeatedly (i.e., continuously or periodically), remove the liquid phase from the reaction zone before the concentration of (i) ethylene glycol exceeds about 20 wt. % of the liquid phase, and (ii) ethylene glycol reaction products exceed 50 wt. % of the total glycol product produced in the liquid phase.

Experimental work has shown that as the ethylene glycol concentration increases in the liquid phase during the course of the reaction, the rate of formation of ethylene glycol is correspondingly diminished. As a consequence it is desirable to operate the process with a minimum allowable concentration of ethylene glycol in order to avoid unduly restricting the rate of ethylene glycol formation. For that reason, the liquid phase in the continuous process should be removed from the reaction zone before the ethylene glycol concentration exceeds 20 wt. % of the weight of the liquid phase. More desirably, the liquid phase from the reaction zone should be withdrawn, either periodically or continuously, before the concentration of ethylene glycol exceeds 15 wt. %. The lower the concentration of ethylene glycol in the liquid phase, the higher will be the rate of ethylene glycol formation. It has also been determined from the experimental work that ethylene glycol reacts with a number of other products formed during the course of the reaction. For example, ethylene glycol will form an acetal with acetaldehyde. Acetaldehyde which is typically formed during the course of this reaction most readily enters into acetal formation. Another reaction product of ethylene glycol which is formed during the reaction is the acetal of glycol aldehyde. Though glycol aldehyde is not readily detectable as a product of the reaction, the acetal is. Still another product is the monomethylether of ethylene glycol.

Many of the aforementioned reaction products of ethylene glycol are useful though less valuable materials than ethylene glycol, and ethylene glycol can certainly be obtained from them, if desired. However, their presence detracts from the economy of the process, because if they are utilized for the purpose of obtaining ethylene glycol, a further step, such as hydrolysis, is required to convert them to ethylene glycol. As a result, it is desirable to control the residence time of the liquid phase during the course of the reaction such that the amount of such ethylene glycol reaction products does not exceed 50 wt. % of the total glycol products which are produced in the liquid phase during the course of the continuous reaction. This number does not include any glycol reaction product which might be utilized as a solvent and introduced into the reaction as such. For example, tetraglyme is a reaction product of ethylene glycol, but it is not construed as one which, when added as a solvent to the reaction, constitutes a reaction product in the above terms. Desirably, the amount of such ethylene glycol reaction products is kept below about 30 wt. % of the total glycol products produced and, most desirably, that amount is kept below 20 wt. %. The most desirable embodiment of the invention would reside when no such ethylene glycol reaction products are formed. However, that is not typically possible in a reaction of this sort.

Although this invention has been described with respect to a number of details, it is not intended that this invention should be limited thereby. Moreover, the examples which follow are intended solely to illustrate a variety, including the most favorable, embodiments of this invention and are not intended in any way to limit the scope and the intent of this invention.

EXAMPLES

In examples 1-4, recorded in Table I below, the following procedure was employed:

A 500 ml stainless steel bomb reactor containing a removable glass liner was charged with a mixture of $Ru_3(CO)_{12}$, solvent and Lewis base as designated below. Carbon monoxide and hydrogen were then added in the designated ratios to the reactor to attain a pressure therein of 3,000 psig (211.95 kg/cm$^2$) at 25° C. The reactor was rocked and the contents heated to the reaction temperature and maintained at this temperature for two hours while rocking the reactor. The pressure was maintained at the specified reaction pressure during the indicated period of the reaction. The reactor was then cooled and vented. The contents of the reactor were removed and analyzed by gas chromatography. Table I directly follows.

TABLE I

| Example Nos. | Millimoles of Ruthenium | Lewis base | Millimoles of Lewis base | Solvent | Milliliters of Solvent | Reaction Temperature, °C. | Reaction Pressure, psig[3] | H₂/CO Ratio | Reaction Period, hours | Grams of Ethylene Glycol Recovered | Grams of Methanol Recovered | Grams of Ethanol Recovered |
|---|---|---|---|---|---|---|---|---|---|---|---|---|
| 1 | 2.34 | LiI | 14.9 | Sulf[1] | 40 | 230 | 5,000 | 1:1 | 2 | .10 | 4.25 | .25 |
| 2 | 2.34 | KI  | 15.0 | Sulf    | 40 | 230 | 5,000 | 1:1 | 2 | .16 | 5.76 | .31 |
| 3 | 2.34 | NaI | 15.0 | Sulf    | 40 | 230 | 5,000 | 1:1 | 2 | .17 | 6.49 | .36 |
| 4 | 2.34 | NaI | 15.0 | NMP[2]  | 50 | 230 | 5,000 | 1:1 | 2 | .16 | 4.12 | .09 |

[1]"Sulf" is an abbreviation for sulfolane.
[2]"NMP" is an abbreviation for N—methylpyrrolidinone.
[3]5,000 psig = 352.57 kg/cm².

The following procedure was employed in the examples recorded in Table II below:

A 150 ml. capacity stainless steel reactor capable of withstanding pressures up to 3,000 atmospheres was charged with a mixture of solvent, ruthenium as triruthenium dodecacarbonyl and Lewis base promoter, as indicated below. The reactor was sealed and charged with a gaseous mixture, containing carbon monoxide and hydrogen in the ratios specified below, to a pressure of 2,500 pounds per square inch gauge (psig) (176.8 kg/cm²). Heat was applied to the reactor and its contents; when the temperature of the mixture inside the reactor reached th designated reaction temperature recited below, as measured by a suitably placed thermocouple, addition of carbon monoxide and hydrogen (H₂:CO=designated mole ratio) was made to bring the pressure to the specified reaction pressure recited below. The temperature (in °C.) was maintained at the desired value for the reported time. During this period of time additional carbon monoxide and hydrogen was added whenever the pressure inside the reactor dropped by more than 500 psig (36.19 kg/cm²). With these added repressurizations the pressure inside the reactor was maintained at the reaction pressure ±500 psig (36.19 kg/cm²) over the entire reaction period.

After the reaction period, the vessel and its contents were cooled to room temperature, the excess gas vented and the reaction product mixture was removed. Analysis of the reaction product mixture was made by gas chromatographic analysis. Table II directly follows.

TABLE II

| Example Nos. | Millimoles of Ruthenium | Lewis base | Millimoles of Lewis base | Solvent | Milliliters of Solvent | Reaction Temperature, °C. | Reaction Pressure, psig (kg/cm²) | H₂/CO Ratio | Reaction Period, hours | Grams of Ethylene Glycol Recovered | Grams of Methanol Recovered | Grams of Ethanol Recovered[11] |
|---|---|---|---|---|---|---|---|---|---|---|---|---|
| 5  | —    | LiI    | 22.4 | Sulf[1]   | 75 | 230 | 5,000 (352.6)   | 1:1 | 4    | —    | —    | —    |
| 6  | 3.51 | LiI    | 22.4 | Sulf[1]   | 75 | 230 | 5,000 (352.6)   | 1:1 | 4    | 1.33 | 3.69 | —    |
| 7  | 3.51 | LiI    | 22.4 | Sulf[1]   | 75 | 230 | 12,500 (879.9)  | 1:1 | 1.15 | 1.42 | 5.36 | 0.14 |
| 8  | 3.51 | LiI    | 22.4 | Sulf[1]   | 75 | 230 | 12,500 (879.9)  | 1:1 | 1.20 | 1.17 | 5.44 | 1.06 |
| 9  | —    | NaI    | 18   | 18-C—6[2] | 75 | 230 | 12,500 (879.9)  | 1:1 | 4    | —    | —    | —    |
| 10 | 3    | NaI    | 6    | 18-C—6[2] | 75 | 230 | 12,500 (879.9)  | 1:1 | 1.75 | 1.68 | 6.26 | 1.0  |
| 11 | 3    | NaI    | 18   | 18-C—6[2] | 75 | 230 | 12,500 (879.9)  | 1:1 | .83  | 1.38 | 7.91 | 1.06 |
| 12 | 3    | NaI    | 36   | 18-C—6[2] | 75 | 230 | 12,500 (879.9)  | 1:1 | .47  | 1.23 | 7.63 | 0.81 |
| 13 | 3    | NaI    | 18   | 18-C—C[2] | 75 | 260 | 12,500 (879.9)  | 1:1 | .33  | 1.20 | 8.30 | 1.88 |
| 14 | 3    | KI     | 3    | 18-C—6[2] | 75 | 230 | 12,500 (879.9)  | 1:1 | 2.30 | 1.51 | 5.75 | 0.70 |
| 15 | 3    | KI     | 6    | 18-C—6[2] | 75 | 230 | 12,500 (879.9)  | 1:1 | 1.50 | 1.38 | 6.53 | 0.71 |
| 16 | 3    | KI     | 12   | 18-C—6[2] | 75 | 230 | 12,500 (879.9)  | 1:1 | .83  | 1.22 | 6.73 | 0.63 |
| 17 | 9    | KI     | 12   | TG[3]     | 75 | 230 | 12,500 (879.9)  | 1:1 | 2.83 | .86  | 6.27 | 0.81 |
| 18 | 3    | NaI    | 6    | TG[3]     | 75 | 230 | 12,500 (879.9)  | 1:1 | 4    | .48  | 6.28 | 1.08 |
| 19 | 3    | LiI    | 24   | TG[3]     | 75 | 260 | 12,500 (879.9)  | 1:1 | 1.30 | .31  | 3.42 | 3.40 |
| 20 | 9    | KOAc[9]| 48   | TG[3]     | 75 | 260 | 12,500 (879.9)  | 1:1 | 2.10 | .08  | 7.13 | —    |
| 21 | 3    | K₃PO₄  | 18   | 18-C—6[2] | 75 | 230 | 12,500 (879.9)  | 1:1 | 3.95 | 1.54 | 5.17 | 1.10 |
| 22 | 3    | PPNI[8]| 3    | TG[3]     | 75 | 230 | 12,500 (879.9)  | 1:1 | 2.33 | .63  | 6.63 | 0.67 |
| 23 | 3    | KI     | 3    | H₂O       | 75 | 230 | 12,500 (879.9)  | 1:1 | 4    | .90  | —    | 1.32 |
| 24 | 3    | KI     | 18   | H₂O       | 75 | 230 | 12,500 (879.9)  | 1:1 | 4    | 1.22 | —    | 2.27 |
| 25 | 9    | KI     | 30   | THF[4]    | 75 | 230 | 12,500           | 1:1 | 4    | .017 | .215 | —    |

TABLE II-continued

| Example Nos. | Millimoles of Ruthenium | Lewis base | Millimoles of Lewis base | Solvent | Milliliters of Solvent | Reaction Temperature, °C. | Reaction Pressure, psig (kg/cm$^2$) | H$_2$/CO Ratio | Reaction Period, hours | Grams of Ethylene Glycol Recovered | Grams of Methanol Recovered | Grams of Ethanol Recovered[11] |
|---|---|---|---|---|---|---|---|---|---|---|---|---|
| 26 | 3.51 | LiI | 15.9 | BL[5] | 75 | 230 | 12,500 (879.9) | 1:1 | 0.9 | .84 | 2.65 | 2.60 |
| 27 | 3 | KI | 18 | 18-C—6[2] | 75 | 230 | 12,500 (879.9) | 1:1 | .75 | 1.29 | 6.58 | 0.12 |
| 28 | 9 | KI | 54 | 18-C—6[2] | 75 | 230 | 12,500 (879.9) | 1:1 | .22 | 2.07 | 7.88 | 1.22 |
| 29 | 15 | KI | 60 | 18-C—6[2] | 75 | 230 | 12,500 (879.9) | 1:1 | .20 | 2.40 | 7.04 | 1.39 |
| 30 | 3 | KI | 18 | NMP[6] | 75 | 230 | 12,500 (879.9) | 1:1 | .65 | .20 | 7.15 | 0.15 |
| 31 | 3 | NaI | 18 | Sulf[1] | 75 | 230 | 12,500 (879.9) | 1:1 | 1.25 | 1.55 | 4.75 | 0.13 |
| 32 | 9 | NaI | 54 | Sulf[1] | 75 | 200 | 12,500 (879.9) | 1:1 | 1.42 | 2.89 | 4.36 | 0.16 |
| 33 | 3 | KOAc[9] | 18 | Sulf[1] | 75 | 230 | 12,500 (879.9) | 1:1 | 4 | .40 | 4.30 | — |
| 34 | 9 | KI | 54 | NMP[6] | 75 | 180 | 12,500 (879.9) | 1:1 | 1.83 | .41 | 2.68 | — |
| 35 | 3 | CsI | 18 | 18-C—6[2] | 75 | 230 | 12,500 (1,054.6) | 1:1 | .70 | 1.15 | 7.83 | 0.88 |
| 36 | 3 | KI | 18 | NMP[6] | 75 | 210 | 15,000 (1,467.2) | 1:1 | .83 | .27 | 5.69 | — |
| 37 | 3 | KI | 18 | NMP[6] | 75 | 180 | 20,000 (879.9) | 1:1 | 2.17 | .33 | 2.84 | — |
| 38 | 3 | KI | 18 | NMP[6] | 75 | 230 | 12,500 (879.9) | 1:1 | .60 | .11 | 7.42 | — |
| 39 | 3 | KI | 18 | 18-C—6[2] | 75 | 230 | 12,500 (879.9) | 1:1 | .82 | 1.13 | 9.38 | 1.07 |
| 40 | 3 | PPNI[8] | 18 | NMP[6] | 75 | 230 | 12,500 (879.9) | 1:1 | .5 | .23 | 6.91 | .31 |
| 41 | 3 | CsI | 18 | NMP[6] | 75 | 230 | 12,500 (879.9) | 1:1 | .63 | .19 | 7.2 | .53 |
| 42 | 3 | NaI | 18 | Sulf[1] | 75 | 230 | 12,500 (879.9) | 1:1 | 1.03 | .79 | 3.16 | .17 |
| 43 | 9 | NaI | 54 | Sulf[1] | 75 | 200 | 12,500 (879.9) | 1:1 | 1.17 | 2.06 | 3.79 | .16 |
| 44 | 9 | KI | 54 | 18-C—6[2] | 75 | 210 | 12,500 (879.9) | 1:1 | .7 | 1.99 | 7.65 | .48 |
| 45 | 15 | KI | 90 | Sulf[1] | 70 | 180 | 12,500 (879.9) | 1:1 | 2 | 2.46 | 2.03 | — |
| 46 | 3 | KI | 90 | Sulf[1] | 70 | 180 | 12,500 (879.9) | 1:1 | 2 | .31 | .64 | — |
| 47 | 5 | KI | 30 | Sulf[1] | 75 | 180 | 12,500 (879.9) | 1:1 | 2 | .66 | .80 | — |
| 48 | 30 | KI | 180 | Sulf[1] | 65 | 180 | 12,500 (879.9) | 1:1 | 1.68 | 4.19 | 2.14 | — |
| 49 | 9 | KI | 59 | 18-C—6[2] | 75 | 180 | 12,500 (879.9) | 2:1 | 1.95 | 2.41 | 4.91 | — |
| 50 | 3 | KI | 18 | Sulf[1] | 75 | 210 | 12,500 (879.9) | 2:1 | 2 | 1.34 | 4.10 | — |
| 51 | 3 | KI | 18 | 18-C—6[2] | 75 | 210 | 12,500 (879.9) | 2:1 | 1.82 | 1.16 | 8.21 | — |
| 52 | 3 | KI | 18 | Sulf[1] | 75 | 210 | 12,500 (879.9) | 1:1 | 2 | 1.39 | 3.40 | — |
| 53 | 3 | KI | 60 | Sulf[1] | 75 | 210 | 12,500 (879.9) | 1:1 | 1.25 | 1.36 | 4.32 | — |
| 54 | 9 | KI | 60 | Sulf[1] | 75 | 180 | 12,500 (879.9) | 1:1 | 2 | 2.39 | 2.49 | — |
| 55 | 9 | KI | 60 | Sulf[1] | 75 | 180 | 12,500 (879.9) | 2:1 | 2 | 2.40 | 3.50 | — |
| 56 | 3 | CsCl | 18 | 18-C—6[2] | 75 | 230 | 12,500 (879.9) | 1:1 | 4 | .30 | 5.61 | — |
| 57 | 9 | KI | 54 | 18-C—6[2] | 75 | 200 | 12,500 (879.9) | 1:1 | .65 | 1.66 | 6.05 | — |
| 58 | 15 | KI | 60 | 18-C—6[2] | 75 | 230 | 12,500 (879.9) | 1:1 | .17 | 1.79 | 6.60 | — |
| 59 | 15 | KI | 60 | 18-C—6[2] | 75 | 260 | 12,500 (879.9) | 1:1 | .13 | .65 | 5.37 | 2.90 |
| 60 | 15 | KI | 60 | 18-C—6[2] | 75 | 200 | 12,500 (879.9) | 1:1 | .47 | 2.96 | 6.86 | — |
| 61 | 30 | KI | 180 | Sulf[1] | 65 | 230 | 12,500 (564.2) | 1:1 | .17 | 2.31 | 5.55 | — |
| 62 | 6 | LiI | 12 | Sulf[1] | 75 | 230 | 8,000 (879.9) | 1:1 | 2.03 | 1.11 | 4.55 | 0.74 |
| 63 | 3 | KI | 18 | Sulf[1] | 75 | 230 | 12,500 (879.9) | 1:1 | 1.08 | 1.15 | 4.91 | — |

TABLE II-continued

| Example Nos. | Millimoles of Ruthenium | Lewis base | Millimoles of Lewis base | Solvent | Milliliters of Solvent | Reaction Temperature, °C. | Reaction Pressure, psig (kg/cm$^2$) | H$_2$/CO Ratio | Reaction Period, hours | Grams of Ethylene Glycol Recovered | Grams of Methanol Recovered | Grams of Ethanol Recovered[11] |
|---|---|---|---|---|---|---|---|---|---|---|---|---|
| 64 | 45 | KI | 180 | Sulf[1] | 65 | 230 | 12,500 (879.9) | 1:1 | 0.12[7] | 2.44 | 5.2 | .32 |
| 65 | 3 | CsI | 18 | 18-C—6[2] | 75 | 230 | 12,500 (879.9) | 1:1 | 0.55 | 0.71 | 5.63 | 0.27 |
| 66 | 3 | BaI$_2$ | 18 | 18-C—6[2] | 75 | 230 | 12,500 (564.2) | 1:1 | 2.0 | 0.01 | 1.77 | 0.34 |
| 67 | 9 | KI | 54 | 18-C—6[2] | 75 | 260 | 8,000 (564.2) | 1:1 | 0.68 | 0.22 | 3.20 | 1.91 |
| 68 | 9 | KI | 54 | 18-C—6[2] | 75 | 280 | 8,000 (564.2) | 1:1 | 0.42 | 0.06 | 2.60 | 1.70 |
| 69 | 3 | NaI | 18 | TG[3] | 75 | 280 | 8,000 (879.9) | 1:1 | 1.72 | 0.13 | 4.67 | 1.92 |
| 70 | 9 | KOAc[9] | 48 | TG[3] | 75 | 260 | 12,500 (879.9) | 1:1 | 2.10 | 0.08 | 7.13 | 1.35 |
| 71 | 3 | CsF | 18 | 18-C—6[2] | 75 | 230 | 12,500 (879.9) | 1:1 | 4 | 0.24 | 5.95 | 0.40 |
| 72 | 3 | K$_2$CO$_3$ | 9 | NMP[6] | 75 | 230 | 12,500 (564.2) | 1:1 | 3.45 | 0.35 | 7.24 | 1.45 |
| 73 | 6 | LiI[10] | 12 | Sulf[1] | 75 | 230 | 8,000 (438.4) | 1:1 | 3.08 | 0.72 | 2.98 | 0.83 |
| 74 | 30 | KI | 180 | Sulf[1] | 75 | 200 | 6,000 | 1:1 | 2.0 | 2.41 | 5.5 | 0.1[12] |

[1]Sulfolane
[2]18-Crown-6 [(CH$_2$CH$_2$O)$_6$]
[3]Tetraglyme [CH$_3$O(CH$_2$CH$_2$O)$_4$CH$_3$]
[4]Tetrahydrofuran
[5]Gamma-butyrolactone
[6]N—methylpyrrolidinone
[7]Rate to ethylene glycol of 5.3 gram moles/liter hr $^{-1}$
[8]Bis(triphenylphosphine)iminium iodide
[9]Potassium acetate
[10]In this example, dicobalt octacarbonyl, Co$_2$(CO)$_8$ (1 millimole), was added to the reaction mixture as a source of tetracarbonyl cobaltate anion.
[11]A dash mark (—) in this column means that ethanol was not determined quantitatively, although its presence was invariably detected by vapor chromatographic analysis
[12]Approximately In some of the examples of Table II, the reaction product was analyzed to determine whether glycerine was present. Each reaction product which was so analyzed was found to contain glycerine. These analyses were made by reacting a sample of the reaction product with bis(trimethylsilyl) trifluoroacetamide. The resulting solution was analyzed by vapor phase chromatography which showed peaks at the correct retention time for the glycerine derivative. The corresponding yields of glycerine were as follows:

| Example No. | Glycerine (grams) |
|---|---|
| 8 | 0.26 |
| 10 | 0.18 |
| 11 | 0.14 |
| 12 | 0.17 |
| 13 | 0.12 |
| 28 | 0.20 |
| 29 | 0.22 |
| 30 | 0.29 |
| 32 | 0.42 |
| 34 | 0.21 |

EXAMPLE 75

A 500 ml stainless steel bomb reactor containing a removable glass liner was charged with a mixture of 0.50 g. Ru$_3$(CO)$_{12}$ in 50 mol of glacial acetic acid. Equimolar amounts of carbon monoxide and hydrogen were then added to the reactor to attain a pressure therein of 3,000 psig (211.95 kg/cm$^2$) at 25° C. The reactor was rocked and the contents heated to 230° C. and maintained at this temperature for two hours while rocking the reactor. The reactor was then cooled and vented. The contents of the reactor were removed and analyzed by gas chromatography. This analysis showed that the following products were produced: 3.25 g. methyl acetate, 1.71 g. ethyl acetate and 0.17 g. ethylene glycol diacetate.

EXAMPLE 76

The procedure of Example 75 was exactly repeated except that the reactor was charged with a mixture of 0.94 g. of Ru(acetylacetonate)$_3$ in 50 ml of glacial acetic acid instead of Ru$_3$(CO)$_{12}$ in 50 ml of glacial acetic acid. Analysis by gas chromatography showed that the following products were produced: 2.77 g. methyl acetate and 0.16 g. ethylene glycol diacetate.

EXAMPLE 77

The procedure of Example 75 was exactly repeated except that a mixture of 0.5 g. Ru$_3$(CO)$_{12}$ in 25 ml of glacial acetic acid and 25 ml ethyl acetate was used instead of Ru$_3$(CO)$_{12}$ in 50 ml of glacial acetic acid. Analysis by gas chromatography showed that the following products were produced: 5.51 g. methyl acetate and 0.06 g. ethylene glycol diacetate.

EXAMPLE 78

The procedure of Example 75 was exactly repeated except that a mixture of 0.5 g. Ru$_3$(CO)$_{12}$ in 25 ml of glacial acetic acid and 25 ml of sulfolane was used instead of Ru$_3$(CO)$_{12}$ in 50 ml of glacial acetic acid. Analysis by gas chromatography showed that the following products were produced: 2.79 g. methyl acetate, 0.49 g. of ethyl acetate and 0.17 g. ethylene glycol diacetate.

EXAMPLE 79

A reactor, as described in Example 75 was charged with a mixture of 0.50 g. Ru$_3$(CO)$_{12}$ in 50 ml of glacial acetic acid. Equimolar amounts of carbon monoxide and hydrogen were then added to the reactor to attain a pressure therein of 3,700 psig (261.17 kg/cm$^2$) at 25° C. The reactor was rocked and the contents heated to 230° C. and maintained at this temperature for two hours while rocking the reactor. The reactor was cooled and vented. The contents of the reactor were removed and analyzed by gas chromatography. This analysis showed that the following products were produced: 4.22 g. methyl acetate and 0.24 g. ethylene glycol diacetate.

EXAMPLE 80

The procedure of Example 75 was exactly repeated except that the reactor was charged with a mixture of 0.50 g Ru$_3$(CO)$_{12}$, 0.8 ml tributylphosphine and 50 ml glacial acetic acid and the contents were pressurized to 3,000 psi and heated to 230° C. and maintained at 230° C. for two hours. Analysis by gas chromatography showed that the following products were produced: 3.26 g methyl acetate, 10.06 g ethyl acetate and 0.04 g ethylene glycol diacetate.

EXAMPLE 81

The procedure of Example 75 was exactly repeated except that the reactor was charged with a mixture of 0.50 g Ru$_3$(CO)$_{12}$, 5 ml of HPF$_6$.[(C$_2$H$_5$)$_2$O] and 50 ml acetic acid and the contents were pressurized to 3,000 psi and heated to 230° C. and maintained at 230° C. for two hours. Analysis by gas chromatography showed that the following products were produced: 5.88 g methyl acetate, 8.40 g ethyl acetate and 0.02 g ethylene glycol diacetate.

EXAMPLE 82

(a) In the reactor described above in the examples of Table II (150 ml high pressure autoclave), 100 ml of tetrahydrofuran (THF) was heated at 230° C. for four hours under 22,500 psi (1,581.9 kg/cm$^2$) of H$_2$/CO present in a 1:1 volume ratio. Analysis of the reaction mixture by vapor phase chromatography showed no ethylene glycol and a small amount of methanol.

(b) After repeating this procedure, except that 20 mmoles of Ru$_3$(CO)$_{12}$ was added, analysis of the reaction mixture by vapor-phase chromatography [Tenax GC (registered trademark of Enka N. V., The Netherlands) column, thermal conductivity detector] showed the major products to be methanol (16.7 area %) and methyl formate (9.7 area %). A peak of 0.56 area % was seen at the correct retention time for ethylene glycol. A sample of this mixture was derivatized by reaction with bis(trimethylsilyl) trifluoroacetamide. Vapor phase chromatography of this mixture showed a peak (0.66 wt. %) at the correct retention time for the ethylene glycol derivative.

(c) Experiment (b) above was repeated except that a pressure of 15,000 psi (1,054.6 kg/cm$^2$) was used and the reaction was held at 250° C. for 13.5 hours. Analysis by vapor-phase chromatography as described in experiment (b) showed a peak of 24.5 area % for methanol and a peak of 4.1 area % for methyl formate. A peak of 0.13 area % was observed at the correct retention time for ethylene glycol. After derivatization as in the previous example, a vapor phase chromatographic peak of 0.11 wt. % was observed at the correct retention time for the ethylene glycol derivative.

EXAMPLE 83

The reactor described above (150 ml stirred high pressure autoclave referred to in the examples of Table II) was charged with 1.4 grams of ruthenium oxide, RuO$_2$.xH$_2$O (from Matthey Bishop, Inc., Malvern, Pa., distributed by Alfa Division, Ventron Corp., Andover, Massachusetts) which is characterized as being composed of 53% Ru by weight. Also added were 3.75 g KHCO$_3$, 60 ml of methanol, and 15 ml of H$_2$O. The mixture was heated at 200° C. for 4 hours under a pressure of 8,000 psig (563.5 kg/cm$^2$) of 2/1 volume ratio of H$_2$/CO. No uptake of gas was observed. Analysis of the solution by vapor phase chromatography showed no alcohol products. Particles of Ru metal were observed in the final mixture. An identical experiment was performed using 1.53 g of Ru$_3$(CO)$_{12}$ instead of RuO$_2$.xH$_2$O. No gas uptake was observed, and no alcohol products were detected. No ruthenium metal or insoluble particles were observed in the final solution.

Though this example fails to show the production of long chain monohydric alcohols, the absence of those products demonstrates the vagaries of heterogeneous catalysis where the reactions are typically dependent on the source and history of the catalyst employed.

EXAMPLE 84

EXAMPLE A

A 150 ml stainless steel reactor, as described before Table II, was charged with a mixture of 30 mmoles of Ru [charged as Ru$_3$(CO)$_{12}$], 120 mmoles of KI, and 75 ml of sulfolane. Equimolar amounts of carbon monoxide and hydrogen were added to the reactor and the reactor then heated to attain a pressure of 12,500 psig at 100° C. for a period of one hour. At the end of this reaction period, the reactor was cooled and vented. The contents of the reactor were analyzed by gas chromatography which showed that 5.19 grams of ethylene glycol has been produced. Substantially all of this amount of ethylene glycol can be removed from the reaction mixture by distillation, and the reaction mixture then reintroduced along with make-up quantities of sulfolane to the reactor to effect further production of ethylene glycol by reaction with a synthesis gas mixture, as described above.

EXAMPLE B

The procedure described in Example A above was repeated, except that 10 grams of ethylene glycol were initially added to the mixture introduced into the reactor, and the reaction was allowed to proceed for four hours, rather than one hour. A net production of 1.4 grams of ethylene glycol was determined by analysis, and glycol derivatives, such as 2-methyl-1,3-dioxolane were formed.

This example demonstrates the diminished rate of ethylene glycol formation which occurs as the concentration of ethylene glycol in the reaction mixture increases.

The repeated removal of ethylene glycol product from the liquid phase mixture, as described in Example A above, can alternatively be carried out continuously in the manner described in the FIGURE.

What is claimed is:

1. The continuous process for making the products methanol, ethylene glycol and ethanol, directly from the reaction of hydrogen and carbon monoxide, which comprises:

(a) establishing and maintaining within a reaction zone a solvent-containing liquid phase comprising solubilized ruthenium carbonyl complex in which the solvent has a dielectric constant of at least 2, determined at 25° C. or at its melting point, which ever is higher;

(b) continuously supplying hydrogen and carbon monoxide in said liquid phase;

(c) maintaining said liquid phase for a sufficient period of time at a temperature and pressure which causes said hydrogen and carbon monoxide to react to produce such products and ethylene glycol further reacts to form ethylene glycol reaction products, said temperature is between about 50° C. and 400° C. and said pressure is between about 500 psia (35.15 kg/cm$^2$) and 15,000 psia (1,054.6 kg/cm$^2$); and (d) repeatedly removing said liquid phase from the reaction zone before the concentration of (i) ethylene glycol exceeds 20 wt. % of said liquid phase and (ii) ethylene glycol reaction products exceed 50 wt. % of the total ethylene glycol and ethylene glycol reaction products produced in said liquid phase.

2. The process of claim 1 wherein a Lewis base promoter of the reaction is provided in the liquid phase.

3. The process of claim 2 wherein the solvent acts as a promoter.

4. The process of claim 3 wherein the solvent is a Lewis base containing compound.

5. The process of claim 2 wherein the solvent is polar.

6. The process of claim 2 wherein the solvent complexes ions.

7. The process of claim 1 wherein the solvent is a carboxylic acid and the products formed are corresponding derivative carboxylates.

8. The process of claim 1 wherein the temperature is between about 100° C. and about 350° C.

9. The process of claim 1 wherein the pressure is between about 500 psia (35.15 kg/cm$^2$) and 12,500 psia (878.84 kg/cm$^2$).

10. The process of claim 1 wherein the pressure is the total pressure of hydrogen and carbon monoxide supplied to said process.

11. The process of claim 5 wherein the solvent is water.

12. The process of claim 5 wherein the solvent is a sulfone.

13. The process of claim 5 wherein the solvent is a lactam.

14. The process of claim 6 wherein the solvent is an ether.

15. The process of claim 14 wherein the solvent is a crown ether.

16. The process of claim 14 wherein the solvent is an alkyl ether of an alkylene glycol.

17. The process of claim 16 wherein the solvent is a dialkyl ether of a polyalkylene glycol.

18. The process of claim 17 wherein the solvent is tetraglyme.

19. The process of claim 5 wherein the solvent is a lactone.

20. The process of claim 19 wherein the solvent is butyrolactone.

21. The process of claim 7 wherein the solvent is acetic acid.

22. The process of claim 2 wherein the promoter is an alkali metal halide.

23. The process of claim 22 wherein the alkali metal halide is an alkali metal iodide.

24. The process of claim 23 wherein the alkali metal iodide is sodium iodide.

25. The process of claim 23 wherein the alkali metal iodide is lithium iodide.

26. The process of claim 23 wherein the alkali metal iodide is potassium iodide.

27. The process of claim 23 wherein the alkali metal iodide is cesium iodide.

28. The process of claim 2 wherein the promoter is an alkali acetate.

29. The process of claim 1 product is continuously removed from said liquid phase in combination with unreacted carbon monoxide and hydrogen.

30. The process of claim 29 wherein unreacted carbon monoxide and hydrogen are recycled to the liquid phase.

31. The process of claim 30 wherein a promoter of the reaction is provided in the liquid phase.

32. The process of claim 2 wherein the amount of promoter provided to the reaction is that amount which achieves a measurable promotional effect.

33. The process of claim 2 wherein the amount of promoter provided in the liquid phase ranges from about 0.1 mole to about $10^6$ moles for each gram atom of ruthenium present.

34. The process of claim 1 wherein the step (d), the liquid phase is removed before (i) the concentration of ethylene glycol exceeds 15 wt. % of said liquid phase and (ii) the concentration of ethylene glycol reaction products exceed 30 wt. % of the ethylene glycol and ethylene glycol reaction products produced.

* * * * *